United States Patent
Ni et al.

(10) Patent No.: US 7,122,639 B2
(45) Date of Patent: Oct. 17, 2006

(54) CHEMOKINE ALPHA-2 ANTIBODIES

(75) Inventors: Jian Ni, Germantown, MD (US); Reiner L. Gentz, Belo Horizonte-MG (BR); Jeffrey Y. Su, Clinton, NJ (US); Haodong Li, Gaithersburg, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 394 days.

(21) Appl. No.: 10/267,900

(22) Filed: Oct. 10, 2002

(65) Prior Publication Data
US 2003/0082748 A1 May 1, 2003

Related U.S. Application Data

(62) Division of application No. 09/238,184, filed on Jan. 27, 1999, now Pat. No. 6,479,633, which is a division of application No. 08/825,556, filed on Mar. 19, 1997, now Pat. No. 5,910,431.

(60) Provisional application No. 60/013,653, filed on Mar. 19, 1996.

(51) Int. Cl.
*A16K 39/395* (2006.01)
*G01N 33/567* (2006.01)
*C07K 1/00* (2006.01)
*C12N 5/12* (2006.01)
*C12P 21/20* (2006.01)

(52) U.S. Cl. ............... 530/388.23; 530/351; 530/387.1; 530/387.9; 514/8; 514/12; 424/9.1; 424/130.1; 424/133.1; 424/136.1; 424/145.1; 435/69.5; 435/326; 435/335; 436/501

(58) Field of Classification Search ................ None
See application file for complete search history.

(56) References Cited

U.S. PATENT DOCUMENTS

| | | | |
|---|---|---|---|
| 4,897,348 A | 1/1990 | Johnson et al. | |
| 5,278,287 A | 1/1994 | Rollins et al. | |
| 5,306,709 A | 4/1994 | Gewirtz et al. | |
| 5,346,689 A | 9/1994 | Peyman et al. | |
| 5,504,003 A | 4/1996 | Li et al. | |
| 5,525,486 A | 6/1996 | Honjo et al. | |
| 5,605,817 A | 2/1997 | Coleman et al. | |
| 5,633,149 A | 5/1997 | Guegler et al. | |
| 5,910,431 A | 6/1999 | Ni et al. | |
| 6,479,633 B1 | 11/2002 | Ni et al. | |

FOREIGN PATENT DOCUMENTS

| | | |
|---|---|---|
| EP | 0488 900 A1 | 6/1992 |
| EP | 0679 716 A1 | 11/1995 |
| WO | WO91/04274 | 4/1991 |
| WO | WO92/06196 | 4/1992 |
| WO | WO94/12537 | 6/1994 |
| WO | WO95/14772 | 6/1995 |
| WO | WO96/17868 | 6/1996 |
| WO | WO96/22374 | 7/1996 |
| WO | WO96/24668 | 8/1996 |
| WO | WO97/41244 | 11/1997 |

OTHER PUBLICATIONS

Baggiolini et al., "Human chemokines: an update, "*Annu. Rev. Immunol.*, 15:675-705 (1997).
Balentien et al., "Recombinant expression, biochemical characterization, and biological activities of the human MGSA/gro protein," *Biochemistry*29(44):10225-10233(Nov. 6, 1990).
Bischoff et al., "Monocyte chemotactic protein 1 is a potent activator of human basophils," *J. Exp. Med.*, 175(5): 1271-5 (May 1, 1992).
Blum et al., "Three human homologs of a murine gene encoding an inhibltor of stem cell proliferation," *DNA Cell Biol.* 9(8):589-602 (Oct. 1990).
Brown et al., "A family of small inducible proteins secreted by leukocytes are members of a new superfamily that includes leukocyte and fibroblast-derived inflammatory agents, growth factors, and indicators of various activation processes," *J Immunol.*. 142(2):679-87 (Jan. 15, 1989).
"Chemokines," in R&D Systems, Minneapolis, MN:80-85 (1994).
Clark-Lewis et al., "Structure-activity relationships of chemokines," *J Leukoc Biol.* 57(5):703-11 (May 1995).
Colditz et al., "In vivo inflammatory activity of neutrophil-activating factor, a novel chemotactic peptide derived from human monocytes," *Am. J. Pathol.* 134(4):755-60 (Apr. 1989).
Gong et al., "Rantes and MCP-3 antagonists bind multiple chemokine receptors," *J. Biol. Chem.* 271(18):10521-20527 (May 3, 1996).

(Continued)

Primary Examiner—Elizabeth Kemmerer
Assistant Examiner—Michael Brannock
(74) Attorney, Agent, or Firm—Human Genome Sciences, Inc.

(57) ABSTRACT

Human chemokine Alpha-2-polypeptides and DNA (RNA) encoding such chemotactic cytokines and a procedure for producing such polypeptides by recombinant techniques is disclosed. Also disclosed are method for utilizing such chemotactic cytokines for the treatment of leukemia, tumors, chronic infections, auto-immune disease, fibrotic disorders, wound healing and psoriasis. Antagonists against such chemotactic cytokines and their use as a therapeutic to treat rheumatoid arthritis, autoimmune and chronic and acute inflammatory and infective diseases, allergic reactions, prostaglandin-independent fever and bone marrow failure are also disclosed. Also disclosed are diagnostic assays for detecting diseases related to mutations in the nucleic acid sequences and altered concentrations of the polypeptides. Also disclosed are diagnostic assays for detecting mutations in the polynucleotides encoding the chemotactic cytokines and for detecting altered levels of the polypeptides in a host.

39 Claims, 4 Drawing Sheets

OTHER PUBLICATIONS

Goodman et al., "Molecular cloning of porcine alveolar macrophage-derived neutrophil chemotactic factors I and II; identification of porcine IL-8 and another intercrine-alpha protein," *Biochemistry*, 31(43):10483-90 (Nov. 3, 1992).

Gress et al., "Hybridization fingerprinting of high-density cDNA-library arrays with cDNA pools derived from whole tissues," *Mamm. Genome*, 3(11):609-19 (1992).

Hara et al., "Molecular cloning and functional characterization of a novel member of the C-C chemokine family," *J. Immunol.* 155(199):5352-8 (Dec. 1, 1995).

Horuk et al., "The Duffy antigen receptor for chemokines: structural analysis and expression in the brain," *J Leukoc Biol.* 59(1):29-38 (Jan. 1996).

Howard et al., "Chemokines: progress toward identifying molecular targets for therapeutic agents," *Trends Biotechnol.* 14(2):46-51 (Feb. 1996).

Jose et al., "Exotaxin: a potent eosinophil chemoattractant cytokine detected in a guinea pig model of allergic airways inflammation," *J. Exp. Med.* 179(3)881-7 (Mar. 1, 1994).

Kuna et al., "Monocyte chemotactic and activating factor is a potent histamine-releasing factor for human basophils," *J Exp Med.* 175(2):489-93 (Feb. 1, 1992).

Kurdowska et al., "Biological and kinetic characterization of recombinant human macrophage inflammatory peptides 2 alpha and beta and comparison with the neutrophil activating peptide 2 and interleukin 8," *Cytokine*6(2):124-34 (Mar. 1994).

Kwon et al., "cDNA sequences of two inducible T-cell genes," *Proc Natl Acad Sci USA*86(6): 1963-7 (Mar. 1989).

Liao et al., "Human Mig chemokine: biochemical and functional characterization," *J Exp Med.* 182(5): 1301-14 (Nov. 1, 1995).

Lukacs et al., "The role of macrophage inflammatory protein 1 alpha in Schistosoma mansoni egg-induced granulomatous inflammation," *J. Exp. Med.*, 177:1551-1559 (Jun. 1, 1993).

Lou et al., "Biologic activities of the murine beta-chemokine TCA3," *J. Immunol.* 153(10):4616-4624 (Nov. 15, 1994).

Matsushima et al., "Purification and characterization of a novel monocyte chemotactic and activating factor produced by a human myelomonocytic cell line," *J. Exp. Med.* 169:1485-1490 (Apr. 1, 1989).

Matsushima et al., "Molecular cloning of a human monocyte-derived neutrophil chemotactic factor (MDNCF) and the induction of MDNCF mRNA by interleukin 1 and tumor necrosis factor," *J. Exp. Med.* 167:1883-1893 (Jun. 1, 1988).

Nakao et al., "Structures of human genes coding for cytokine LD78 and their expression," *Mol. Cell. Biol.* 10(7) :3646-3658 (Jul. 1990).

Obaru et al., "A cDNA clone used to study mRNA inducible in human tonsillar lymphocytes by a tumor promoter," *J Biochem* (Tokyo 99(3):885-894 (Mar. 1986).

Proost et al., "Human and bovine granulocyte chemotactic protein-2: complete amino acid sequence and functional characterization as chemokines," *Biochemistry*32(38):10170-10177 (Sep. 28, 1993).

Proudfoot et al., "Extension of recombinant human RANTES by the retention of the initiating methionine produces a potent antagonist," *J. Biol. Chem.* 271(5):2599-2603 (Feb. 2, 1996).

Schall, "Biology of the RANTES/SIS cytokine family," *Cytokine*3(3):165-183 (May 1991).

Schulz-Knappe et al., "HCC-1, a novel chemokine from human plasma," *J. Exp. Med.* 183(1):295-299 (Jan. 1, 1996).

Sudo et al., "2058 expressed sequence tags (ESTs) from a human fetal lung cDNA library," *Genomics*24:276-279 (Nov. 15, 1994).

Szabo et al., "Chemokine class differences in binding to the Duffy antigen-erythrocyte chemokine receptor," *J. Biol. Chem.* 270(43):25348-25351 (Oct. 27, 1995).

Taub et al., "Chemokines, inflammation and the Immune system," *Ther. Immunol.* 1:229-246 (Aug. 1994).

Genbank Accession No: N73929, Hillier et al., "za74a05.s1 Soares_fetal_lung $_{13}$ NbHL19W Homo sapiens cDNA clone Image:298256 3" (Mar. 19, 1996).

Zipfel et al., "Mitogenic activation of human T cells induces two closely related genes which share structural similarities with a new family of secreted factors," *J. Immunol.* 142(5):1582-1590 (Mar. 1, 1989).

English language abstract of EP0488 900A1 (92-185765/199223).

Genbank Accession No: F08989, "HSC2VD112 normalized infant brain cDNA Homo sapiens cDNA clone c-2vd11 3" (Feb. 23, 1995).

Genbank Accession No: F08988, Auffray et al., "HSC2VD102 normalized infant brain cDNA Homo sapiens cDNA clone c-2vd10 3" (Feb. 23, 1995).

Genbank Accession No: R40176, Hillier et al., "yf70d10.s1 Soares infant brain 1 NIB Homo sapiens cDNA clone Image:27769 3" (May 22, 1995).

Wells et al., "Selectivity and antagonism of chemokine receptors," *J. Leukoc. Biol.* 59(1):53-60 (Jan., 1996).

Genbank Accession No: W59562, Marra et al., "md72g02.r1 Soares mouse embryo NbME13.5 14.5 Mus musculus cDNA clone Image:373970 5" (Jun. 6, 1996).

Genbank Accession No: W97325, Marra et al., "mg08b11.r1 Soares mouse embryo NbME13.5 14.5 Mus musculus cDNA clone Image:423165 5" (Jul. 16, 1996).

Genbank Accession No: C00476, Okubo, "HUMGS0007866, Human Gene Signature, 3'-directed cDNA sequence" (Jul. 12, 1996).

Genbank Accession No: AA014463, Marra et al., "ml64e05.r1 Soares mouse embryo NbME13.5 14.5 Mus musculus cDNA clone Image:468320 5" (Jul. 31, 1996).

Genbank Accession No: N92825, Hillier et al., "zb67e02.s1 Soares_fetal_lung_NbHL19W Homo sapiens cDNA clone Image:308666 3" (Aug. 20, 1996).

Genbank Accession No: AA041600, Marra et al., "mj06f10.r1 Soares mouse embryo NbME13.5 14.5 Mus musculus cDNA clone Image:475339 5" (Sep. 3, 1996).

Genbank Accession No: AA050284, Marra et al., "mj10h11.r1 Soares mouse embryo NbME13.5 14.5 Mus musculus cDNA clone Image:475749 5" (Sep. 9, 1996).

Genbank Accession No: AA048803, Marra et al., "mj48f07.r1 Soares mouse embryo NbME13.5 14.5 Mus musculus cDNA clone Image:479365 5" (Sep. 9, 1996).

Genbank Accession No: W72294, Hillier et al., "zd60c06.s1 Soares_fetal_heart_NbHH19W Homo sapiens cDNA clone Image:345034 3" (Oct. 16, 1996).

Genbank Accession No: W76320, Hillier et al., "zd60c06.r1 Soares_fetal_heart_NbHH19W Homo sapiens cDNA clone Image:345034 5" (Oct. 16, 1996).

Genbank accession No: AA111146, Marra et al. "mp10d02.r1 Life Tech mouse embryo 8 5dpc 10664019 Mus musculus cDNA clone Image:568803 5" (Nov. 6, 1996).

Genbank Accession No: AA111198, Marra et al. "mp10b02.r1 Life Tech mouse embryo 8 5dpc 10664019 Mus musculus cDNA clone Image:568779 5" (Nov. 6, 1996).

Genbank Accession No: AA498558, Marra et al., "vh44e03.r1 Barstead mouse pooled organs MPLRB4 Mus musculus cDNA clone Image:889852 5" (Jul. 1, 1997).

Genbank Accession No: AA505654, NCI-CGAP, "nh82b09.s1 NCI_CGAP_BR1.1 Homo sapiens cDNA clone Image:964985 3" (Aug. 18, 1997).

Genbank Accession No: AA514740, NCI-CGAP, "ni08a04.s1 NCI_CGAP _Br2 Homo sapiens cDNA clone Image:967374 3" (Aug. 18, 1997).

Genbank Accession No: AA584399, NCI-CGAP, "nn77d12.s1 NCI_CGAP_Co9 Homo sapiens cDNA clone Image:1089911 3" (Sep. 8, 1997).

Genbank Accession No: AA600802, NCI-CGAP, "np44e09.s1 NCI_CGAP_Br1.1 Homo sapiens cDNA clone Image:1129192 3" (Oct. 1, 1997).

Genbank Accession No: AA621994, NCI-CGAP, "nq43e08.s1 NCI_CGAP_Co10 Homo sapiens cDNA clone Image:1146662 3" (Oct. 21, 1997).

Genbank Accession No: AA643952, NCI-CGAP, "np42h05.s1 NCI_CGAP_Br1.1 Homo sapiens cDNA clone Image:1129017 3" (Oct. 27, 1997).

Genbank Accession No: AA649666, NCI-CGAP, "ns44g10.s1 NCI_CGAP_Alv1 Homo sapiens cDNA clone Image:1186530" (Nov. 13, 1997).
Genbank Accession No: AA886723, NCI-CGAP, "oj52h02.s1 NCI-CGAP_Kid3 Homo sapiens cDNA clone Image:1601971 3" (Mar. 30, 1998).
Genbank Accession No: AA863280, NCI-CGAP, "og93a04.s1 NCI_CGAP_Kid5 Homo sapiens cDNA clone Image:1455822 3" (Apr. 29, 1998).
Genbank Accession No: X65378, Gress et al., "HSB45EST Human fetal brain cDNA (T.M. Gress) Homo sapiens cDNA clone B45" (Apr. 30, 1998).
Genbank Accession No: AA865643, NCI-CGAP, "og89a10.s1 NCI_CGAP_Kid5 Homo sapiens cDNA clone Image:1455450 3" (Apr. 29, 1998).
Genbank Accession No: AA863442, NCI-CGAP, "oh05e08.s1 NCI_CGAP_Kid3 Homo sapiens cDNA clone Image:1456934 3" (May 13, 1998).
Genbank Accession No: AA863354, NCI-CGAP, "oh04e07.s1 NCI_CGAP_Kid3 Homo sapiens cDNA clone Image:1456836 3" (May 13, 1998).
Genbank Accession No: AA887491, NCI-CGAP, "oj54c08.s1 NCI_CGAP_Kid3 Homo sapiens cDNA clone Image:1502126 3" (Jun. 9, 1998).
Genbank Accession No: AA907750, NCI-CGAP, "om13h04.s1 Soares_NFL_T_GBC_S1 Homo sapiens cDNA clone" (Jun. 10, 1998).
Genbank Accession No: W92533, Hillier et al., "ze03h09.r1 Soares_fetal_heart_NbHH19W Homo sapiens cDNA clone Image:357953 5" (Nov. 25, 1996).
Genbank Accession No: W94666, Hillier et al., "ze03h09.s1 Soares_fetal_heart_NbHH19W Homo sapiens cDNA clone Image:357953 3" (Nov. 25, 1996).
Genbank Accession No: AA017998, Marra et al.,"mh47h11.r1 Soares mouse placenta 4NbMP13.5 14.5 Mus musculus cDNA clone Image:445701 5"(Jan. 21, 1997).
Genbank Accession No: AA013634, Marra et al., "mh10h08.r1 Soares mouse placenta 4NbMP13.5 14.5 Mus musculus cDNA clone Image:442143 5" (Jan. 21, 1997).
Genbank Accession No: AA024564, Hillier et al.,"ze74e06.r1 Soares_fetal_heart_NbHH19W Homo sapiens cDNA clone Image:364738 5" (Jan. 30, 1997).
Geneseq Accession No: T25671, Matsubara et al.,"Human gene signature HUMGS07866" (Oct. 9, 1996).
Geneseq Accession No: X10538, Hudson et al., "Human biallelic polymorphic DNA fragment WI-13424" (Mar. 30, 1999).
Genbank Accession No: AI848074, Bonaldo et al., "Ul-M-AP1-agk-b-04-0-Ul.s1 NIH_BMAP_MST_N Mus musculus cDNA clone" (Jul. 15, 1999).
Genbank Accession No: AI848074, Bonaldo et al., "Ul-M-AK0-adi-f-01-0-Ul.s1 NIH_BMAP_MHY Mus musculus cDNA clone" (Jul. 14, 1999).
Genbank Accession No: AI838231, Bonaldo et al., "Ul-M-AL0-abx-e-03-0-Ul.s1 NIH_BMAP_MCO Mus musculus cDNA clone" (Jul. 14, 1999).
Genbank Accession No: AI043862, Bonaldo et al., "Ul-R-C0-jm·g-02-0-Ul.s1 Ul-R-C0 Rattus norvegicus cDNA clone" (Jul. 5, 1999).
Genbank Accession No: AI835287, Bonaldo et al.,"Ul-M-AQ0-aab-e-05-0-Ul.s1 NIH_ BMAP_MHI Mus musculus cDNA clone" (Jul. 14, 1999).
Genbank Accession No: AI835155, Bonaldo et al.,"Ul-M-AQ0-aaf-e-02-0-Ul.s1 NIH_BMAP_MHI Mus musculus cDNA clone"(Jul. 14, 1999).
Genbank Accession No: AI037414, Marra et al., "ub52e01.r1 Soares_mammary_gland_NbMMG Mus musculus cDNA clone Image:1381368 5" (Jun. 26, 1998).
Genbank Accession No: AA245464, Marra et al., "mx01c03.r1 Soares mouse NML Mus musculus cDNA clone Image:678916 5" (Mar. 10, 1997).
Genbank Accession No: AI717263, Bonaldo et al., "Ul-R-Y0-aca-a-10-0-Ul.s1 Ul-R-Y0 Rattus norvegicus cDNA clone" (Jun. 10, 1999).

Genbank Accession No: W34624, Marra et al., "mc31c07.r1 Soares mouse p3NMF19.5 Mus musculus cDNA clone Image:350124 5" (Sep. 11, 1996).
Genbank Accession No: W70315, Hillier et al., "zd68e07.s1 Soares_fetal_heart_NbHH19W Homo sapiens cDNA clone Image:345828 3'similar to gb:J05016 Protein Disulfide Isomerase-Related Protein Precursor (Human)" (Oct. 17, 1996).
Genbank Accession No: AI576567, Bonaldo et al., "Ul-R-G0-uq-g-11-0-Ul.s1 Ul-R-G0 Rattus norvegicus cDNA clone" (Apr. 5, 1999).
Cao et al., "Molecular Cloning and Characterization of a Novel CXC Chemokine Macrophage Inflammatory Protein-2y Chemoattractant for Human Neutrophils and Dendritic Cells," *J. Immunol.*, 165(5):2588-2595 (Sep. 2000).
Sugiyama et al., "Membrane topology analysis of *Escherichia coli* mannitol permease by using a nested-deletion method to create *mtla-phoA* fusions," PNAS, 88:9603-9607 (Nov. 1991).
Munro et al., "Use of peptide tagging to detect proteins expressed from cloned genes: deletion mapping functional domains of *Drosophila* hsp70,"*EMBO J.*3(13):3087-3093 (Dec. 1984).
Pollard et al., "Truncated variants of gp120 bind CD4 with high affinity and suggest a minimum CD4 binding region," *EMBO J.*, 11(2):585-591 (1992).
Johnston et al., "Differential Roles of Selectins and the $\alpha_4$-Integrin in Acute, Subacute, and Chronic Leukocyte Recruitment in Vivo," *J. Immunol.*, 159(9):4514-4523 (Nov. 1997).
Lauffenburger et al., "Measurement of Leukocyte Motility and Chemotaxis Parameters With a Linear Under-Agarose Migration Assay," *J. Immunol.*, 131(2):940-947 (Aug. 1983).
McLaughlin et al., "A quantitative in vitro assay of polymorphonuclear leukocyte migration through human amnion membrane utilizing $^{111}$In-oxine,"*J. Immunol. Methods*, 95:89-98 (1986).
Grimstad et al., "A New Assay for Leukocyte Chemotaxis Using Cell Retrieval, Electronic Particle Counting and Flow Cytometry," *J. Immunol. Methods*, 49:215-233 (1982).
Buettner et al., "Measurement of leukocyte motility and chemotaxis parameters with the Millipore filter assay," *J. Immunol. Methods*, 123:25-37 (1989).
Watanabe et al., "Very Rapid Assay of Polymorphonuclear Leukocyte Chemotaxis in Vitro,"*J. Pharmacol. Methods*, 22:13-18 (1989).
Watanabe et al., "Inflammatory and Immunological nature of atherosclerosis," *Intl. J. Cardiology*, 54:S51-S60 (1996).
Bush et al., "Cytokine expression and synovial pathology in the initiation and spontaneous resolution phases of adjuvant arthritis: Interleukin-17 expression is upregulated in early disease," *Clin. Exp. Immunol.*, 123:487-495 (2001).
Hromas et al., "Cloning of BRAK, a novel divergent CXC chemokine preferentially expressed in normal versus malignant cells," *Biochem Biophys Res Commun.* 255(3):703-6 (Feb. 24, 1999).
Sleeman et al., "B cell- and monocyte-activating chemokine (BMAC), a novel non-ELR alpha-chemokine." *Int Immunol.* 12(5): 677-89 (May 2000).
Frederick et al., "In vivo expression of the novel CXC chemokine BRAK in normal and cancerous human tissue," *Am. J. Pathol.* 156(6):1937-50 (Jun. 2000).
Kurth et al., "Monocyte selectivity and tissue localization suggests a role for breast and kidney-expressed chemokine (BRAK) in macrophage development," *J Exp Med.* 194(6):855-61 (Sep. 17, 2001).
Muller Wa, "New Mechanisms and pathways for monocyte recruitment," *J Exp Med.* 194(9):F47-51 (Nov. 5, 2001).
Shellenberger et al., "BRAK/CXCL14 is a potent Inhibitor of angiogenesis and a chemotactic factor for Immature dendritic cells," *Cancer Res.* 64(22):8262-70 (Nov. 15, 2004).
Shurin et al., "Lose of new chemokine CXCL14 in tumor tissue is associated with low infiltration by dendritic cells (DC), while restoration of human CXCL14 expression in tumor cells causes attraction of DC both In vitro and In vivo," *J Immunol.* 174(9):5490-8 (May 1, 2005).

```
              10                    30                    50
ACGAGCTCCGGGCCGCCGCTCCGACGGGCCAGCGCCCTCCCCATGTCCCTGCTCCCACGC
                                              M  S  L  L  P  R 70                    90                   110
CGCGCCCCTCCGGTCAGCATGAGGCTCCTGGCGGCCGCGCTGCTCCTGCTGCTGCTGGCG
 R  A  P  P  V  S  M  R  L  L  A  A  A  L  L  L  L  L  L  A 130                   150                   170
CTGTACACCGCGCGTGTGGACGGGTCCAAATGCAAGTGCTCCCGGAAGGGACCCAAGATC
 L  Y  T  A  R  V  D  G  S  K  C  K  C  S  R  K  G  P  K  I 190                   210                   230
CGCTACAGCGACGTGAAGAAGCTGGAAATGAAGCCAAAGTACCCGCACTGCGAGGAGAAG
 R  Y  S  D  V  K  K  L  E  M  K  P  K  Y  P  H  C  E  E  K 250                   270                   290
ATGGTTATCATCACCACCAAGAGCGTGTCCAGGTACCGAGGTCAGGAGCACTGCCTGCAC
 M  V  I  I  T  T  K  S  V  S  R  Y  R  G  Q  E  H  C  L  H 310                   330                   350
CCCAAGCTGCAGAGCACCAAGCGCTTCATCAAGTGGTACAACGCCTGGAACGAGAAGCGC
 P  K  L  Q  S  T  K  R  F  I  K  W  Y  N  A  W  N  E  K  R 370                   390                   410
AGGTTCTACGAAGAATAGGGTGAAAAACCTCAGAAGGGAAAACTCCAAACCAGTTGGGAG
 R  F  Y  E  E  *

430                   450
ACTTGTGGCAAAGGAACTTTGCAGATTAAAAAAAAAAAAAA
```

FIG.1

```
         10                  30                  50
ACGAGCTCCGGGCCGCCGCTCCGACGGGCCAGCGCCCTCCCCATGTCCCTGCTCCCACGC 70                  90                 110
CGCGCCCCTCCGGTCAGCATGAGGCTCCTGGCGGCCGCGCTGCTCCTGCTGCTGCTGGCG
                  M  R  L  L  A  A  A  L  L  L  L  L  L  A 130                 150                 170
CTGTACACCGCGCGTGTGGACGGGTCCAAATGCAAGTGCTCCCGGAAGGGACCCAAGATC
 L  Y  T  A  R  V  D  G  S  K  C  K  C  S  R  K  G  P  K  I 190                 210                 230
CGCTACAGCGACGTGAAGAAGCTGGAAATGAAGCCAAAGTACCCGCACTGCGAGGAGAAG
 R  Y  S  D  V  K  K  L  E  M  K  P  K  Y  P  H  C  E  E  K 250                 270                 290
ATGGTTATCATCACCACCAAGAGCGTGTCCAGGTACCGAGGTCAGGAGCACTGCCTGCAC
 M  V  I  I  T  T  K  S  V  S  R  Y  R  G  Q  E  H  C  L  H 310                 330                 350
CCCAAGCTGCAGAGCACCAAGCGCTTCATCAAGTGGTACAACGCCTGGAACGAGAAGCGC
 P  K  L  Q  S  T  K  R  F  I  K  W  Y  N  A  W  N  E  K  R 370                 390                 410
AGGTTCTACGAAGAATAGGGTGAAAAACCTCAGAAGGGAAAACTCCAAACCAGTTGGGAG
 R  F  Y  E  E  *

430                 450
ACTTGTGGCAAAGGAACTTTGCAGATTAAAAAAAAAAAAAA
```

FIG.2

```
  9 PPVSMRLLAAALLLLLLLALYTARVDGS.......KCKCSRKGPKIRYSDV 51
    :|...|||.|||||||| : |.: .::       :|.| :. |:: :.::
  2 APPTRRLLNAALLLLLLLMATSHQPSGTVVARELRCQCLKTLPRVDFENI 51

52 KKLEMKPKYPHCEEKMVIITTKSVSRYRGQEHCLHPKLQSTKRFIKWYNA 101
    ..|.:.|. |||.:. || | |.    ||| ||:|. .. .::|...
 52 QSLTVTPPGPHCTQTEVIATLKD.....GQEVCLNPQAPRLQKIIQKLLK 96

102 WNE 104

97 SPS 99
```

FIG.3

```
  1 MRLLAAALLLLLLLALYTARVDGS.......KCKCSRKGPKIRYSDV 39
    .|||.|||||||| : |.: .::       :|.| :. |:: :.::
  6 RRLLNAALLLLLLLMATSHQPSGTVVARELRCQCLKTLPRVDFENI 51

40 KKLEMKPKYPHCEEKMVIITTKSVSRYRGQEHCLHPKLQSTKRFIKWYNA 89
    ..|.:.|. |||.:. || | |.    ||| ||:|. .. .::|...
 52 QSLTVTPPGPHCTQTEVIATLKD.....GQEVCLNPQAPRLQKIIQKLLK 96

90 WNE 92

97 SPS 99
```

FIG.4

SEQUENCE LISTING

<160> NUMBER OF SEQ ID NOS: 10

<210> SEQ ID NO 1
<211> LENGTH: 461
<212> TYPE: DNA
<213> ORGANISM: Homo sapiens

<400> SEQUENCE: 1

```
acgagctccg ggccgccgct ccgacgggcc agcgccctcc ccatgtccct gctcccacgc      60
cgcgcccctc cggtcagcat gaggctcctg gcggccgcgc tgctcctgct gctgctggcg     120
ctgtacaccg cgcgtgtgga cgggtccaaa tgcaagtgct cccggaaggg acccaagatc     180
cgctacagcg acgtgaagaa gctggaaatg aagccaaagt acccgcactg cgaggagaag     240
atggttatca tcaccaccaa gagcgtgtcc aggtaccgag gtcaggagca ctgcctgcac     300
cccaagctgc agagcaccaa cgcgttcatc aagtggtaca acgcctggaa cgagaagcgc     360
aggttctacg aagaataggg tgaaaaacct cagaagggaa aactccaaac cagttgggag     420
acttgtggca aggaactttt gcagattaaa aaaaaaaaa a                          461
```

<210> SEQ ID NO 2
<211> LENGTH: 111
<212> TYPE: PRT
<213> ORGANISM: Homo sapiens

<400> SEQUENCE: 2

```
Met Ser Leu Leu Pro Arg Arg Ala Pro Pro Val Ser Met Arg Leu Leu
1               5                   10                  15

Ala Ala Ala Leu Leu Leu Leu Leu Ala Leu Tyr Thr Ala Arg Val
            20                  25                  30

Asp Gly Ser Lys Cys Lys Cys Ser Arg Lys Gly Pro Lys Ile Arg Tyr
        35                  40                  45

Ser Asp Val Lys Lys Leu Glu Met Lys Pro Lys Tyr Pro His Cys Glu
    50                  55                  60

Glu Lys Met Val Ile Ile Thr Thr Lys Ser Val Ser Arg Tyr Arg Gly
65                  70                  75                  80

Gln Glu His Cys Leu His Pro Lys Leu Gln Ser Thr Lys Arg Phe Ile
                85                  90                  95

Lys Trp Tyr Asn Ala Trp Asn Glu Lys Arg Arg Phe Tyr Glu Glu
            100                 105                 110
```

<210> SEQ ID NO 3
<211> LENGTH: 99
<212> TYPE: PRT
<213> ORGANISM: Homo sapiens

<400> SEQUENCE: 3

```
Met Arg Leu Leu Ala Ala Ala Leu Leu Leu Leu Leu Ala Leu Tyr
1               5                   10                  15

Thr Ala Arg Val Asp Gly Ser Lys Cys Lys Cys Ser Arg Lys Gly Pro
            20                  25                  30

Lys Ile Arg Tyr Ser Asp Val Lys Lys Leu Glu Met Lys Pro Lys Tyr
        35                  40                  45

Pro His Cys Glu Glu Lys Met Val Ile Ile Thr Thr Lys Ser Val Ser
    50                  55                  60

Arg Tyr Arg Gly Gln Glu His Cys Leu His Pro Lys Leu Gln Ser Thr
65                  70                  75                  80
```

```
Lys Arg Phe Ile Lys Trp Tyr Asn Ala Trp Asn Glu Lys Arg Arg Phe
                85                  90                  95

Tyr Glu Glu

<210> SEQ ID NO 4
<211> LENGTH: 98
<212> TYPE: PRT
<213> ORGANISM: Cricetulus griseus

<400> SEQUENCE: 4

Ala Pro Pro Thr Arg Arg Leu Leu Asn Ala Ala Leu Leu Leu Leu Leu
1               5                   10                  15

Leu Leu Met Ala Thr Ser His Gln Pro Ser Gly Thr Val Val Ala Arg
                20                  25                  30

Glu Leu Arg Cys Gln Cys Leu Lys Thr Leu Pro Arg Val Asp Phe Glu
            35                  40                  45

Asn Ile Gln Ser Leu Thr Val Thr Pro Pro Gly Pro His Cys Thr Gln
        50                  55                  60

Thr Glu Val Ile Ala Thr Leu Lys Asp Gly Gln Glu Val Cys Leu Asn
65                  70                  75                  80

Pro Gln Ala Pro Arg Leu Gln Lys Ile Ile Gln Lys Leu Leu Lys Ser
                85                  90                  95

Pro Ser

<210> SEQ ID NO 5
<211> LENGTH: 26
<212> TYPE: DNA
<213> ORGANISM: Artificial sequence
<220> FEATURE:
<223> OTHER INFORMATION: Primer sequence containing a SphI restriction
      site

<400> SEQUENCE: 5
cccgcatgcc cgcgcgtgtg gacggg                                          26

<210> SEQ ID NO 6
<211> LENGTH: 27
<212> TYPE: DNA
<213> ORGANISM: Artificial sequence
<220> FEATURE:
<223> OTHER INFORMATION: Primer sequence containing a BamHl restriction
      site

<400> SEQUENCE: 6
cccggatccc tattcttcgt agaacct                                         27

<210> SEQ ID NO 7
<211> LENGTH: 29
<212> TYPE: DNA
<213> ORGANISM: Artificial sequence
<220> FEATURE:
<223> OTHER INFORMATION: Primer sequence containing a BamHI restriction
      enzyme site

<400> SEQUENCE: 7
gccggatccg ccatcatgtc cctgctccc                                       29

<210> SEQ ID NO 8
<211> LENGTH: 28
<212> TYPE: DNA
<213> ORGANISM: Artificial sequence
<220> FEATURE:
```

```
<223> OTHER INFORMATION: Primer containing an XbaI restriction site

<400> SEQUENCE: 8
cgcgtctaga ctattcttcg tagaacct                                         28

<210> SEQ ID NO 9
<211> LENGTH: 30
<212> TYPE: DNA
<213> ORGANISM: Artificial sequence
<220> FEATURE:
<223> OTHER INFORMATION: Primer sequence containing a BamHI site

<400> SEQUENCE: 9
aaaggatcca tgtccctgct cccacgccgc                                       30

<210> SEQ ID NO 10
<211> LENGTH: 57
<212> TYPE: DNA
<213> ORGANISM: Artificial sequence
<220> FEATURE:
<223> OTHER INFORMATION: Primer sequence containing an XbaI site

<400> SEQUENCE: 10
cgctctagat caagcgtagt ctgggacgtc gtatgggtat tcttcgtaga acctgcg        57
```

CHEMOKINE ALPHA-2 ANTIBODIES

CROSS REFERENCE TO RELATED APPLICATIONS

This application is a divisional of U.S. application Ser. No. 09/238,184, filed Jan. 27, 1999 (now U.S. Pat. No. 6,479,633, issued Nov. 12, 2002), which is a divisional of U.S. application Ser. No. 08/825,556, filed Mar. 19, 1997 (now U.S. Pat. No. 5,910,431, issued Jun. 8, 1999), which claims benefit under 35 U.S.C. § 119 (e) to U.S. application No. 60/013,653, filed Mar. 19, 1996, each of which is hereby incorporated by reference in its entirety.

FIELD OF THE INVENTION

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of human chemokine alpha-2, hereinafter referred to as "CKα-2".

BACKGROUND OF THE INVENTION

The ability to control the migration and "trafficking" of various cell types is controlled by a subset of factors, or proteins, among which chemokines are an example.

Chemokines, also referred to as intercrine cytokines, are a subfamily of structurally and functionally related chemotactic cytokines. These molecules are 8–10 kd in size. In general, chemokines exhibit 20% to 75% homology at the amino acid level and are characterized by four conserved cysteine residues that form two disulfide bonds. Based on the arrangement of the first two cysteine residues, chemokines have been classified into two subfamilies, alpha and beta. In the alpha subfamily, the first two cysteines are separated by one amino acid and hence are referred to as the "C—X—C" subfamily. In the beta subfamily, the two cysteines are in an adjacent position and are, therefore, referred to as the "C—C" subfamily. Thus far, at least eight different members of this family have been identified in humans.

The intercrine cytokines exhibit a wide variety of functions. A hallmark feature is their ability to elicit chemotactic migration of distinct cell types, including monocytes, neutrophils, T lymphocytes, basophils and fibroblasts. Many chemokines have proinflammatory activity and are involved in multiple steps during an inflammatory reaction. These activities include stimulation of histamine release, lysosomal enzyme and leukotriene release, increased adherence of target immune cells to endothelial cells, enhanced binding of complement proteins, induced expression of granulocyte adhesion molecules and complement receptors, and respiratory burst. In addition to their involvement in inflammation, certain chemokines have been shown to exhibit other activities. For example, macrophage inflammatory protein 1 (MIP-1) is able to suppress hematopoietic stem cell proliferation, platelet factor-4 (PF-4) is a potent inhibitor of endothelial cell growth, interleukin-3 (IL-8) promotes proliferation of keratinocytes, and GRO is an autocrine growth factor for melanoma cells.

In light of the diverse biological activities, it is not surprising that chemokines have been implicated in a number of physiological and disease conditions, including lymphocyte trafficking, wound healing, hematopoietic regulation and immunological disorders such as allergy, asthma and arthritis.

Members of the "C—C" branch exert their effects on the following cells: eosinophils which destroy parasites to lessen parasitic infection and cause chronic inflammation in the airways of the respiratory system; macrophages which suppress tumor formation in vertebrates; and basophils which release histamine which plays a role in allergic inflammation. However, members of one branch may exert an effect on cells which are normally responsive to the other branch of chemokines and, therefore, no precise role can be attached to the members of the branches.

While members of the C—C branch act predominantly on mononuclear cells and members of the C—X—C branch act predominantly on neutrophils a distinct chemoattractant property cannot be assigned to a chemokine based on this guideline. Some chemokines from one family show characteristics of the other.

The polypeptide of the present invention has the conserved cysteine residues of the "C—X—C" region, and have amino acid sequence homology to known chemokines.

Clearly, there is a need for factors that regulate the migration of distinct cell types and their roles in dysfunction and disease. There is a need, therefore, for identification and characterization of such factors that regulate the migration of cells, particularly cells of the immune system, and which can play a role in preventing, ameliorating or correcting dysfunctions or diseases.

SUMMARY OF THE INVENTION

Toward these ends, and others, it is an object of the present invention to provide polypeptides, inter alia, that have been identified as novel CKα-2 by homology between the amino acid sequence set out in both FIG. 1 (SEQ ID NO:2) and FIG. 2 (SEQ ID NO:3) and known amino acid sequences of other proteins such as Chinese hamster GRO protein set out in FIGS. 3 and 4 (SEQ ID NO:4).

It is a further object of the invention, moreover, to provide polynucleotides that encode CKα-2, particularly polynucleotides that encode the polypeptides herein designated CKα-2.

In a particularly preferred embodiment of the aspect of the invention the polynucleotide comprise the regions encoding the human CKα-2 polypeptides in the sequences set out in FIGS. 1 and 2 (SEQ ID NO:1).

In accordance with this aspect of the present invention there is provided an isolated nucleic acid molecule encoding mature polypeptides expressed by the human cDNA contained in ATCC Deposit No. 97400 deposited on Jan. 2, 1996.

In accordance with this aspect of the invention there are provided isolated nucleic acid molecules encoding human CKα-2 polypeptides, including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of human CKα-2.

It also is an object of the invention to provide CKα-2 polypeptides, particularly human CKα-2 polypeptides, that may be employed for therapeutic purposes, for example, to treat and/or prevent tumors, chronic infections, leukemia, T-cell mediated auto-immune diseases, parasitic infections, psoriasis, asthama, allergy, to regulate hematopoiesis, to stimulate growth factor activity, to inhibit angiogenesis and to promote wound healing.

In accordance with this aspect of the invention there are provided novel polypeptides of human origin referred to herein as CKα-2 as well as biologically, diagnostically or therapeutically useful fragments, variants and derivatives thereof, variants and derivatives of the fragments, and analogs of the foregoing.

Among the particularly preferred embodiments of this aspect of the invention are variants of human CKα-2 encoded by naturally occurring alleles of the human CKα-2 gene.

It is another object of the invention to provide a process for producing the aforementioned polypeptides, polypeptide fragments, variants and derivatives, fragments of the variants and derivatives, and analogs of the foregoing. In a preferred embodiment of this aspect of the invention there are provided methods for producing the aforementioned CKα-2 polypeptides comprising culturing host cells having expressibly incorporated therein an exogenously-derived human CKα-2-encoding polynucleotide under conditions for expression of a human CKα-2 polypeptide in the host and then recovering the expressed polypeptide.

In accordance with another object the invention there are provided products, compositions, processes and methods that utilize the aforementioned polypeptides and polynucleotides for research, biological, clinical and therapeutic purposes, inter alia.

In accordance with certain preferred embodiments of this aspect of the invention, there are provided products, compositions and methods, inter alia, for, among other things: assessing CKα-2 expression in cells by determining CKα-2 polypeptides or CKα-2-encoding mRNA; assaying genetic variation and aberrations, such as defects, in CKα-2 genes; and administering a CKα-2 polypeptide or polynucleotide to an organism to augment CKα-2 function or remediate CKα-2 dysfunction.

In accordance with certain preferred embodiments of this and other aspects of the invention there are provided probes that hybridize to human CKα-2 sequences.

In certain additional preferred embodiments of this aspect of the invention there are provided antibodies against CKα-2 polypeptides. In certain particularly preferred embodiments in this regard, the antibodies are highly selective for human CKα-2.

In accordance with another aspect of the present invention, there are provided CKα-2 agonists. Among preferred agonists are molecules that mimic CKα-2, that bind to CKα-2-binding molecules or receptor molecules, and that elicit or augment CKα-2-induced responses. Also among preferred agonists are molecules that interact with CKα-2 or CKα-2 polypeptides, or with other modulators of CKα-2 activities, and thereby potentiate or augment an effect of CKα-2 or more than one effect of CKα-2.

In accordance with yet another aspect of the present invention, there are provided CKα-2 antagonists. Among preferred antagonists are those which mimic CKα-2 so as to bind to CKα-2 receptors or binding molecules but not elicit a CKα-2-induced response or more than one CKα-2-induced response. Also among preferred antagonists are molecules that bind to or interact with CKα-2 so as to inhibit an effect of CKα-2 or more than one effect of CKα-2 or which prevent expression of CKα-2, for the treatment of disease and dysfunction mediated by CKα-2.

In a further aspect of the invention there are provided compositions comprising a CKα-2 polynucleotide or a CKα-2 polypeptide for administration to cells in vitro, to cells ex vivo and to cells in vivo, or to a multicellular organism. In certain particularly preferred embodiments of this aspect of the invention, the compositions comprise a CKα-2 polynucleotide for expression of a CKα-2 polypeptide in a host organism for treatment of disease. Particularly preferred in this regard is expression in a human patient for treatment of a dysfunction associated with aberrant endogenous activity of CKα-2.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1 shows the nucleotide (SEQ ID NO:1) and deduced amino acid (SEQ ID NO:2) sequence of a human CKα-2 protein initiated from the AUG codon located at positions 43 to 45 in SEQ ID NO:1. The protein has a predicted leader sequence of about 28 amino acid residues (underlined) and a deduced molecular weight of about 10 kilodaltons (kDa).

FIG. 2 shows the nucleotide (SEQ ID NO:1) and deduced amino acid (SEQ ID NO:3) sequence of a human CKα-2 protein initiated from the AUG codon located at positions 79 to 81 in SEQ ID NO:1. The protein has a predicted leader sequence of about 16 amino acid residues (underlined) and a deduced molecular weight of about 8.6 kDa.

FIG. 3 shows the regions of similarity between amino acid sequences of CKα-2 of SEQ ID NO:2 and Chinese hamster GRO polypeptide (SEQ ID NO:4).

FIG. 4 shows the regions of similarity between amino acid sequences of CKα-2 of SEQ ID NO:3 and Chinese hamster GRO polypeptide (SEQ ID NO:4).

DETAILED DESCRIPTION OF THE PREFERRED EMBODIMENTS

Figure 5:
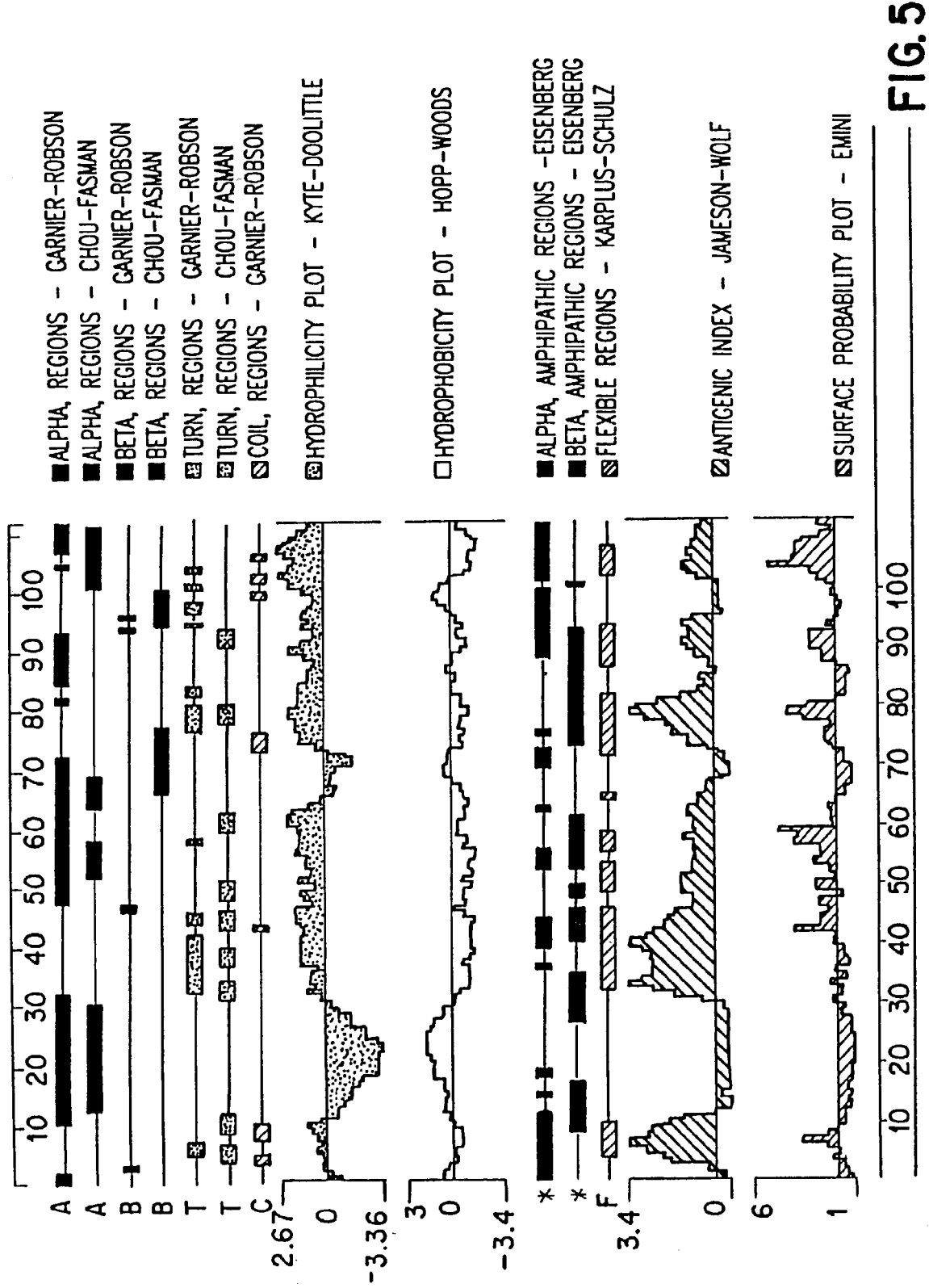
FIG. 5 shows structural and functional features of the CKα-2 shown in SEQ ID NO: 2 deduced by the indicated techniques, as a function of amino acid sequence.

The following illustrative explanations are provided to facilitate understanding of certain terms used frequently herein, particularly in the examples. The explanations are provided as a convenience and are not limitative of the invention.

The term "digestion" of DNA refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 μg of plasmid or DNA fragment is digested with about 2 units of enzyme in about 20 μl of reaction buffer. For the purpose of isolating DNA fragments for plasmid construction, typically 5 to 50

µg of DNA are digested with 20 to 250 units of enzyme in proportionately larger volumes. Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well known methods that are routine for those skilled in the art.

The term "genetic element" generally means a polynucleotide comprising a region that encodes a polypeptide or a region that regulates transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, a molecule physically independent of the host cell genome. They may be comprised within mini-chromosomes, such as those that arise during amplification of transfected DNA by methotrexate selection in eukaryotic cells. Genetic elements also may be comprised within a host cell genome; not in their natural state but, rather, following manipulation such as isolation, cloning and introduction into a host cell in the form of purified DNA or in a vector, among others.

The term "isolated" means altered "by the hand of man" from its natural state; i.e., that, if it occurs in nature, it has been changed or removed from its original environment, or both. For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

The term "ligation" refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., *Molecular Cloning, A Laboratory Manual,* 2nd Ed.; Cold Spring Harbor Laboratory Press, Cold Spring Harbor, N.Y. (1989) and Maniatis et al., pg. 146, as cited below.

The term "oligonucleotide(s)" refers to relatively short polynucleotides. Often the term refers to single-stranded deoxyribonucleotide, but it can refer as well to single or double-stranded ribonucleotides, RNA:DNA hybrids and double-stranded DNAs, among others.

Oligonucleotides, such as single stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

The term "plasmids" generally are designated herein by a lower case p preceded and/or followed by capital letters and/or numbers, in accordance with standard naming conventions that are familiar to those of skill in the art.

Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

The term "polynucleotide(s)" generally refers to any polyribonucleotide or polydeoxribonucleotide, which may be unmodified RNA or DNA or modified RNA or DNA. Thus, for instance, polynucleotides as used herein refers to, among others, single and double-stranded DNA, DNA that is a mixture of single- and double-stranded regions, single- and double-stranded RNA, and RNA that is mixture of single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

The term "polypeptides", as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance, Creighton, T. E., *Proteins—Structure And Molecular Properties*, 2nd Ed., W. H. Freeman and Company, New York (1993). Many detailed reviews are available on this subject, such as, for example, those provided by Wold, F., "Posttranslational Protein Modifications: Perspectives and Prospects," in *Posttranslational Covalent Modification of Proteins*, Johnson, B. C., ed., Academic Press, New York (1983), pp. 1–12; Seifter et al., "Analysis for protein modifications and nonprotein cofactors," *Meth. Enzymol.* 182:626–546 (1990), and Rattan et al., *Ann. N.Y. Acad. Sci.* 663:48–62 (1992).

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylating host, generally a eukaryotic cell. Insect cell often carry out the same postrranslational glycosylations as mammalian cells and, for this reason, insect cell expression systems have been developed to express efficiently mammalian proteins having native patterns of glycosylation, inter alia. Similar considerations apply to other modifications.

It will be appreciated that the same type of modification may be present in the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

The term "variant(s)" of polynucleotides or polypeptides, as the term is used herein, are polynucleotides or polypeptides that differ from a reference polynucleotide or polypeptide, respectively. Variants in this sense are described below and elsewhere in the present disclosure in greater detail.

A polynucleotide variant is a variant that differs in nucleotide sequence from another, reference polynucleotide. Generally, differences are limited so that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence, of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

A polypeptide variant is a variant that differs in amino acid sequence from another, reference polypeptide. Generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination.

The term "receptor molecule", as used herein, refers to molecules which bind or interact specifically with CKα-2 polypeptides of the present invention, including not only classic receptors, which are preferred, but also other molecules that specifically bind to or interact with polypeptides of the invention (which also may be referred to as "binding molecules" and "interaction molecules," respectively, and as "CKα-2 binding molecules" and "CKα-2 interaction molecules." Binding between polypeptides of the invention and such molecules, including receptor or binding or interaction molecules may be exclusive to polypeptides of the invention, which is a very highly preferred, or it may be highly specific for polypeptides of the invention, which is highly preferred, or it may be highly specific to a group of proteins that includes polypeptides of the invention, which is preferred, or it may be specific to several groups of proteins at least one of which includes polypeptides of the invention. Receptors also may be non-naturally occurring, such as antibodies and antibody-derived reagents that bind specifically to polypeptides of the invention.

The present invention relates to novel CKα-2 polypeptides and polynucleotides, among other things, as described in greater detail below. In particular, the invention relates to polypeptides and polynucleotides of novel human CKα-2, which is related by amino acid sequence homology to Chinese hamster GRO. The invention relates especially to CKα-2 polypeptides having the nucleotide and amino acid sequences set out in FIGS. 1 and 2, and to the CKα-2 nucleotide and amino acid sequences of the human cDNA in the deposited clone. It will be appreciated that the nucleotide and amino acid sequences set out in FIGS. 1 and 2 were obtained by sequencing the human cDNA of the deposited clone. Hence, the sequence of the deposited clone is controlling as to any discrepancies between these sequences and any reference to the sequences of FIGS. 1 and 2 include reference to the sequence of the human cDNA of the deposited clone.

In accordance with one aspect of the present invention, there are provided isolated polynucleotides which encode the CKα-2 polypeptides having the deduced amino acid sequences of FIGS. 1 and 2.

Using the information provided herein, such as the polynucleotide sequence set out in FIG. 1 or FIG. 2, a polynucleotide of the present invention encoding human CKα-2 polypeptides may be obtained using standard cloning and screening procedures, such as those for cloning cDNAs using mRNA from cells of human tissue as starting material. Illustrative of the invention, the polynucleotide set out in FIGS. 1 and 2 was discovered in a cDNA library derived from cells of a human six week old embryo.

The human CKα-2 polypeptides of the invention are structurally related to other proteins of the chemokine family, as shown by the results of sequencing the human cDNA encoding CKα-2 in the deposited clone. The cDNA sequence thus obtained is set out in FIGS. 1 and 2 and is believed to contain two possible open reading frames. One open reading frame, shown in FIG. 1, encodes a protein of about 111 amino acid residues (SEQ ID NO:2) with a deduced molecular weight of about 10 kDa and a putative leader sequence of about 28 amino acids. This protein exhibits greatest homology to Chinese hamster GRO (SEQ ID NO:4), among known proteins (FIG. 3). The entire CKα-2 protein of FIG. 1 has about 32% identity and about 50% similarity with the amino acid sequence of the Chinese hamster GRO protein.

The second open reading frame, shown in FIG. 2, encodes a protein of about 99 amino acid residues (SEQ ID NO:3) with a deduced molecular weight of about 8.6 kDa and a putative leader sequence of about 16 amino acids. This protein exhibits greatest homology to Chinese hamster GRO (SEQ ID NO:4), among known proteins (FIG. 4).

A number of eukaryotic mRNAs have been shown to encode more than one transcript based on the utilization of different AUG codons. In eukaryotic cells the selection of an AUG codon as the translational start point is determined by both the location of that codon in relationship to the cap at the 5' end of the mRNA molecule and the nucleotides surrounding the codon. If the first AUG codon is poorly situated for the initiation of transcription, many ribosomes will skip over this codon and proceed to another AUG codon in the mRNA molecule. As a result, multiple translation products can be produced from the same mRNA molecule. The cDNA encoding the CKα-2 polypeptides of the present invention is believed to produce from such a mRNA molecule. Further, two translation products, shown in SEQ ID NO:2 and SEQ ID NO:3, are believed to be produced. These products vary in respect to the length of putative leader sequence.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single stranded. Single-stranded DNA may be the coding strand, also known as the sense strand, or it may be the non-coding strand, also referred to as the anti-sense strand.

The coding sequence which encodes the polypeptides may be identical to the coding sequences of the polynucleotide shown in FIGS. 1 and 2. It also may be a polynucleotide with a different sequence, which, as a result of the redundancy (degeneracy) of the genetic code, encodes the polypeptides of the DNA of FIGS. 1 and 2.

Polynucleotides of the present invention which encode the polypeptides of FIGS. 1 and 2 may include, but are not limited to the coding sequence for the mature polypeptide, by itself; the coding sequence for the mature polypeptide and additional coding sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci. (USA)* 86:821–824 (1989), for instance, hexa-histidine provides for convenient purification of the fusion protein. The HA tag corresponds to an epitope derived of influenza hemagglutinin protein, which has been described by Wilson et al., *Cell* 37:767 (1984), for instance.

In accordance with the foregoing, the term "polynucleotide encoding a polypeptide" as used herein encompasses polynucleotides which include a sequence encoding a polypeptide of the present invention, particularly the human CKα-2 polypeptides having the amino acid sequences set out in FIGS. 1 and 2. The term encompasses polynucleotides that include a single continuous region or discontinuous regions encoding the polypeptide (for example, interrupted by introns) together with additional regions, that also may contain coding and/or non-coding sequences.

The present invention further relates to variants of the herein above described polynucleotides which encode for fragments, analogs and derivatives of the polypeptides having the deduced amino acid sequences of FIGS. 1 and 2. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequences of CKα-2 set out in FIGS. 1 and 2; variants, analogs, derivatives and fragments thereof, and fragments of the variants, analogs and derivatives.

Further particularly preferred in this regard are polynucleotides encoding CKα-2 variants, analogs, derivatives and fragments, and variants, analogs and derivatives of the fragments, which have the amino acid sequence of the CKα-2 polypeptides of FIGS. 1 and 2 in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the CKα-2. Also especially preferred in this regard are conservative substitutions. Most highly preferred are polynucleotides encoding polypeptides having the amino acid sequences of FIGS. 1 and 2, substitutions.

Further preferred embodiments of the invention are polynucleotides that are at least 70% identical to a polynucleotide encoding the CKα-2 polypeptides having the amino acid sequences set out in FIGS. 1 and 2, and polynucleotides which are complementary to such polynucleotides. Alternatively, most highly preferred are polynucleotides that comprise a region that is at least 80% identical to a polynucleotide encoding the CKα-2 polypeptides of the human cDNA of the deposited clone and polynucleotides complementary thereto. In this regard, polynucleotides at least 90% identical to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Particularly preferred embodiments in this respect, moreover, are polynucleotides which encode polypeptides which retain substantially the same biological function or activity as the mature polypeptide encoded by the human cDNA of FIGS. 1 and 2.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probe for cDNA and genomic DNA to isolate full-length cDNAs and genomic clones encoding CKα-2 polypeptides and to isolate cDNA and genomic clones of other genes that have a high sequence similarity to the human CKα-2 gene. Such probes generally will comprise at least 15 bases. Preferably, such probes will have at least 30 bases and may have at least 50 bases.

For example, the coding region of the CKα-2 gene may be isolated by screening using the known DNA sequence to synthesize an oligonucleotide probe. A labeled oligonucleotide having a sequence complementary to that of a gene of the present invention is then used to screen a library of human cDNA, genomic DNA or mRNA to determine which members of the library the probe hybridizes to.

The polynucleotides and polypeptides of the present invention may be employed as research reagents and materials for discovery of treatments and diagnostics to human disease, as further discussed herein relating to polynucleotide assays, inter alia.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

A deposit containing a human CKα-2 cDNA has been deposited with the American Type Culture Collection, as noted above. Also as noted above, the cDNA deposit is referred to herein as "the deposited clone" or as "the cDNA of the deposited clone." The deposited clone was deposited with the American Type Culture Collection, 12301 Park Lawn Drive, Rockville, Md. 20852, USA, on Jan. 2, 1996, and assigned ATCC Deposit No. 97400. The deposited material is a pBluescrip SK (−) plasmid (Stratagene, La Jolla, Calif.) that contains the full length CKα-2 cDNA, referred to as "PF250" upon deposit.

The deposit has been made under the terms of the Budapest Treaty on the international recognition of the deposit of micro-organisms for purposes of patent procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. § 112. The sequence of the polynucleotides contained in the deposited material, as well as the amino acid sequence of the polypeptide encoded thereby, are controlling in the event of any conflict with any description of sequences herein. A license may be required to make, use or sell the deposited materials, and no such license is hereby granted.

The present invention further relates to a human CKα-2 polypeptides which have the deduced amino acid sequences of FIGS. 1 and 2.

The invention also relates to fragments, analogs and derivatives of these polypeptides. The terms "fragment," "derivative" and "analog" when referring to the polypeptides of FIGS. 1 and 2, means a polypeptide which retains essentially the same biological function or activity as such polypeptide. Thus, an analog includes a proprotein which can be activated by cleavage of the proprotein portion to produce an active mature polypeptide.

The polypeptides of the present invention may be recombinant polypeptides, natural polypeptides or synthetic polypeptides. In certain preferred embodiments it is a recombinant polypeptide.

The fragment, derivative or analog of the polypeptides of FIGS. 1 and 2 may be (I) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequences of CKα-2 set out in FIGS. 1 and 2, variants, analogs, derivatives and fragments thereof, and variants, analogs and derivatives of the fragments. Alternatively, particularly preferred embodiments of the invention in this regard are polypeptides having the amino acid sequence of the CKα-2 polypeptides encoded by the cDNA in the deposited clone, variants, analogs, derivatives and fragments thereof, and variants, analogs and derivatives of the fragments.

Among preferred variants are those that vary from a reference by conservative amino acid substitution. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and gln, exchange of the basic residues Lys and Arg and replacements among the aromatic residues Phe, Tyr.

The polypeptides and polynucleotides of the present invention are preferably provided in an isolated form, and preferably are purified to homogeneity.

The polypeptides of the present invention include the polypeptide of SEQ ID NO:2 or SEQ ID NO:3 (in particular the mature polypeptide) as well as polypeptides which have at least 70% similarity (preferably at least 70% identity) to the polypeptide of SEQ ID NO:2 or SEQ ID NO:3 and more preferably at least 90% similarity (more preferably at least 90% identity) to the polypeptide of SEQ ID NO:2 or SEQ ID NO:3 and still more preferably at least 95% similarity (still more preferably at least 95% identity) to the polypeptide of SEQ ID NO:2 or SEQ ID NO:3 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

Also among preferred embodiments of this aspect of the present invention are polypeptides comprising fragments of CKα-2, most particularly fragments of CKα-2 having the amino acid sequences set out in FIGS. 1 and 2, or having the amino acid sequences of the CKα-2 proteins encoded by the deposited clone, and fragments of variants and derivatives of the CKα-2 proteins of FIGS. 1 and 2 or encoded by the deposited clone. In this regard a fragment is a polypeptide having an amino acid sequence that entirely is the same as part but not all of the amino acid sequence of the aforementioned CKα-2 polypeptides and variants or derivatives thereof. As representative examples of polypeptide fragments of the invention, there may be mentioned those which have from about 30 to about 111 amino acids.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a CKα-2 polypeptide of the present comprised within a precursor polypeptide designed for expression in a host and having heterologous pre and pro-polypeptide regions fused to the amino terminus of the CKα-2 fragment and an additional region fused to the carboxyl terminus of the fragment. Therefore, fragments in one aspect of the meaning intended herein, refers to the portion or portions of a fusion polypeptide or fusion protein derived from CKα-2.

In this context about includes the particularly recited range and ranges larger or smaller by several, a few, 5, 4, 3, 2 or 1 amino acid at either extreme or at both extremes. For instance, about 30 amino acids in this context means a polypeptide fragment of 30 plus or minus several, a few, 5, 4, 3, 2 or 1 amino acids to 111 plus or minus several a few, 5, 4, 3, 2 or 1 amino acid residues, i.e., ranges as broad as 30 minus several amino acids to 111 plus several amino acids to as narrow as 30 plus several amino acids to 111 minus several amino acids.

Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments from about 30 to about 111 amino acids.

Among especially preferred fragments of the invention are truncation mutants of CKα-2. Truncation mutants include CKα-2 polypeptides having the amino acid sequences of FIGS. 1 and 2, or of the deposited clone, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally.

Also preferred in this aspect of the invention are fragments characterized by structural or functional attributes of CKα-2. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of CKα-2.

Certain preferred regions in these regards are set out in FIG. 5, and include, but are not limited to, regions of the aforementioned types identified by analysis of the amino acid sequences set out in FIGS. 1 and 2. As set out in FIG. 5, such preferred regions include Garnier-Robson alpha-regions, beta-regions, turn-regions and coil-regions. Chou-Fasman alpha-regions, beta-regions and turn-regions, Kyte-Doolittle hydrophilic regions and hydrophilic regions, Eisenberg alpha and beta amphipathic regions, Karplus-Schulz flexible regions, Emini surface-forming regions and Jameson-Wold high antigenic index regions.

Among highly preferred fragments in this regard are those that comprise regions of CKα-2 that combine several structural features, such as several of the features set out above. In this regard, the regions defined by the residues about 30 to 111 of FIG. 1 (amino acids 2 to 83 in SEQ ID NO:2) and by the residues about 18 to 99 of FIG. 2 (amino acids 6 to 83 in SEQ ID NO:3), which all are characterized by amino acid compositions highly characteristic of turn-regions, hydrophilic regions, flexible-regions, surface-forming regions, and high antigenic index-regions, are especially highly preferred regions. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of CKα-2. Most highly preferred in this regard are fragments that have a chemical, biological or other activity of CKα-2, including those with a similar activity or an improved activity, or with a decreased undesirable activity. Highly preferred in this regard are fragments that contain regions that are homologs in sequence, or in position, or in both sequence and to active regions of related polypeptides, such as the related polypeptides set out in FIGS. 3 and 4, which include Chinese hamster GRO. Among particularly preferred fragments in these regards are truncation mutants, as discussed above.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspond to the preferred fragments, as discussed above.

The present invention also related to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced along or with other polynucleotides. Such other polynucleotides may be introduced independently, co-introduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques.

In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those of skill, are set forth in great detail in Sambrook et al. cited elsewhere herein.

The DNA sequence in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRS to name just a few of the well-known promoters. It will be understood that numerous promoters not mentioned are suitable for use in this aspect of the invention are well known and readily may be employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as *E. coli,* Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Hosts for a great variety of expression constructs are well known, and those of skill will be enabled by the present disclosure readily to select a host for expression a polypeptides in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are PWLNEO, pSV2CAT, pOG44, PXTI and pSG available from Stratagene; and pSVK3, PBPV, PMSG and PSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("cat") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the E. coli lacI and lacZ promoters, the T3 and T7 promoters, the gpt promoter, the lambda PR, PL promoters and the trp promoter. Among known eukaryotic promoters suitable in this regard are the CMV immediate early promoter, the HSV thymidine kinase promoter, the early and late SV40 promoters, the promoters of retroviral LTRS, such as those of the Rous sarcoma virus ("RSV"), and metallothionein promoters, such as the mouse metallothionein-I promoter.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell.

Introduction of the construct into the host cell can be effected by calcium phosphate transfection. DEAE-dextran mediated transfection, cationic lipid-mediated transfection, electroporation, transduction, infection or other methods. Such methods are described in many standard laboratory manuals, such as Davis et al., *Basic Methods in Molecular Biology* (1986).

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual,* 2nd Ed., Cold Spring Harbor Laboratory Press, Cold Spring Harbor, N.Y. (1989).

Generally, recombinant expression vectors will include origins of replication, a promoter derived from a highly-expressed gene to direct transcription of a downstream structural sequence, and a selectable marker to permit isolation of vector containing cells after exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of *E. coli* and the trp1 gene of *S. cerevisiae.*

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Suitable prokaryotic hosts for propagation, maintenance or expression of polynucleotides and polypeptides in accordance with the invention include *Escherichia coli, Bacillus* subtilis and *Salmonella typhimurium*. Various species of Pseudomonas, Streptomyces, and Staphylococcus are suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis. USA). These pBR322 "backbone" sections are combined with an appropriate promoter and the structural sequence to be expressed.

Following transformation of a suitable host strain and growth of the host strain to an appropriate cell density, where the selected promoter is inducible it is induced by appropriate means (e.g., temperature shift or exposure to chemical inducer) and cells are cultured for an additional period. Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can be employed for expression, as well. Examples of mammalian expression systems include the COS-7 lines of monkey kidney fibroblast, described in Gluzman et al., *Cell* 23:175 (1981). Other cell lines capable of expressing a compatible vector include for example, the C127, 3T3, CHO, HeLa, human kidney 293 and BHK cell lines.

Mammalian expression vectors will comprise an origin of replication, a suitable promoter and enhancer, and also any necessary ribosome binding sites, polyadenylation sites, splice donor and acceptor sites, transcriptional termination sequences, and 5' flanking non-transcribed sequences that are necessary for expression. In certain preferred embodiments in this regard DNA sequences derived from the SV40 splice sites, and the SV40 polyadenylation sites are used for required non-transcribed genetic elements of these types.

The CKα-2 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host mediated processes.

CKα-2 polynucleotides and polypeptides may be used in accordance with the present invention for a variety of applications, particularly those that make use of the chemical and biological properties of CKα-2. Additional applications relate to diagnosis and to treatment of disorders of cells, tissues and organisms. These aspects of the invention are illustrated further by the following discussion.

This invention is also related to the use of the CKα-2 polynucleotides to detect complementary polynucleotides such as, for example, as a diagnostic reagent. Detection of a mutated form of CKα-2 associated with a dysfunction will provide a diagnostic tool that can add or define a diagnosis of a disease or susceptibility to a disease which results from under-expression, over-expression or altered expression of CKα-2. Individuals carrying mutations in the human CKα-2 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. PCR (Saiki et al., *Nature* 324:163–166 (1986)). RNA or cDNA may also be used in the same ways. As an example, PCR primers complementary to the nucleic acid encoding CKα-2 can be used to identify and analyze CKα-2 expression and mutations. For example, deletions and insertions can be detected by a change in size of the amplified product in comparison to the normal genotype. Point mutations can be identified by hybridizing amplified DNA to radiolabeled CKα-2 RNA or alternatively, radiolabeled CKα-2 antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing fortnamide gradient gels in which the mobilities of different DNA fragments are retarded in the gel at different positions according to their specific melting or partial melting temperatures (see, e.g., Myers et al., *Science* 230:1242 (1985)).

Sequence changes at specific locations also may be revealed by nuclease protection assays, such as RNase and S1 protection or the chemical cleavage method (e.g., Cotton et al., *Proc. Natl. Acad. Sci.* (USA) 85:4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP")) and Southern blotting of genomic DNA. In addition to more conventional gel-electrophoresis and DNA sequencing, mutations also can be detected by in situ analysis.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a CKα-2 gene. This can be accomplished using a variety of well known techniques and libraries, which generally are available commercially. The genomic DNA is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with cDNA as short as 50 or 60. For a review of this technique, see Verma et al., *Human Chromosomes: A Manual Of Basic Techniques,* Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man,* available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The present invention also relates to a diagnostic assays such as quantitative and diagnostic assays for detecting levels of CKα-2 protein in cells and tissues, including determination of normal and abnormal levels. Thus, for instance, a diagnostic assay in accordance with the invention for detecting over-expression of CKα-2 protein compared to normal control tissue samples may be used to detect the presence of a tumor, for example. Assay techniques that can be used to determine levels of a protein, such as a CKα-2 protein of the present invention, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to CKα-2, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

To carry out an ELISA a sample is removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any CKα-2 proteins attached to the polystyrene dish. Unbound monoclonal antibody is washed out with buffer. The reporter antibody linked to horseradish peroxidase is placed in the dish resulting in binding of the reporter antibody to any monoclonal antibody bound to CKα-2 through the primary and secondary antibodies, produces a colored reaction product. The amount of color developed in a given time period indicates the amount of CKα-2 protein present in the sample. Quantitative results typically are obtained by reference to a standard curve.

A competition assay may be employed wherein antibodies specific to CKα-2 attached to a solid support and labeled CKα-2 and a sample derived from the host are passed over the solid support and the amount of label detected attached to the solid support can be correlated to a quantity of CKα-2 in the sample.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides.

Such antibodies can then be used to isolate the polypeptide from tissue expressing that polypeptide.

The antibodies may be employed to isolate or to identify clones expressing the polypeptide or purify a polypeptide of the present invention by attachment to a solid support for isolation and/or purification by affinity chromatography.

For preparation of monoclonal antibodies, any technique which provides antibodies produced by continuous cell line cultures can be used. Examples include the hybridoma technique (Kohler, G. and Milstein, C., *Nature* 256:495–497 (1975)), the trioma technique, the human B-cell hybridoma technique (Kozbor et al., *Immunology Today* 4:72 (1983)) and the EBV-hybridoma technique to produce human monoclonal antibodies (Cole et al., in *Monoclonal Antibodies And Cancer Therapy*, Alan R. Liss, Inc. (1985), pp. 77–96).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

The above-described antibodies may be employed to isolate the polypeptides of the present invention by attachment of the antibody to a solid support and performing affinity chromatography by passing the polypeptide desired to be purified over the column and recovering the purified polypeptide.

Thus, among others, CKα-2 may be employed to inhibit bone marrow stem cell colony formation as adjunct protective treatment during cancer chemotherapy and for leukemia.

CKα-2 may also be employed to inhibit epidermal keratinocyte proliferation for treatment of psoriasis, which is characterized by keratinocyte hyper-proliferation.

CKα-2 may also be employed to treat solid tumors by stimulating the invasion and activation of host defense cells, e.g., cytotoxic T cells and macrophages and by inhibiting the angiogenesis of tumors. They may also be employed to enhance host defenses against resistant chronic and acute infections, for example, mycobacterial infections via the attraction and activation of microbicidal leukocytes.

CKα-2 may also be employed to inhibit T cell proliferation by the inhibition of IL-2 biosynthesis for the treatment of T-cell mediated auto-immune diseases and lymphocytic leukemias.

CKα-2 may also be employed to stimulate wound healing, both via the recruitment of debris clearing and connective tissue promoting inflammatory cells and also via its control of excessive TGFβ-mediated fibrosis. In this same manner, CKα-2 may also be employed to treat other fibrotic disorders, including liver cirrhosis, osteoarthritis and pulmonary fibrosis.

CKα-2 also increases the presence of eosinophils which have the distinctive function of killing the larvae of parasites that invade tissues, as in schistosomiasis, trichinosis and ascariasis.

It may also be employed to regulate hematopoiesis, by regulating the activation and differentiation of various hematopoietic progenitor cells, for example, to release mature leukocytes from the bone marrow following chemotherapy.

This invention also provides a method for identification of molecules, such as receptor molecules, that bind CKα-2. Genes encoding proteins that bind CKα-2, such as receptor proteins, can be identified by numerous methods known to those of skill in the art, for example, ligand panning and FACS sorting. Such methods are described in many laboratory manuals such as, for instance, Coligan et al., *Current Protocols in Immunology* 1(2):Chapter 5 (1991).

For instance, expression cloning may be employed for this purpose. To this end polyadenylated RNA is prepared from a cell responsive to CKα-2, a cDNA library is created from this RNA, the library is divided into pools and the pools are transfected individually into cells that are not responsive to CKα-1. The transfected cells then are exposed to labeled CKα-2. (CKα-2 can be labeled by a variety of well-known techniques including standard methods of radio-iodination or inclusion of a recognition site for a site-specific protein kinase.) Following exposure, the cells are fixed and binding of CKα-2 is determined. These procedures conveniently are carried out on glass slides.

Pools are identified of cDNA that produced CKα-2-binding cells. Sub-pools are prepared from these positives, transfected into host cells and screened as described above. Using an iterative sub-pooling and re-screening process, one or more single clones that encode the putative binding molecule, such as a receptor molecule, can be isolated.

Alternatively a labeled ligand can be photoaffinity linked to a cell extract, such as a membrane or a membrane extract, prepared from cells that express a molecule that it binds, such as a receptor molecule. Cross-linked material is resolved by polyacrylamide gel electrophoresis ("PAGE") and exposed to X-ray film. The labeled complex containing the ligand-receptor can be excised, resolved into peptide fragments, and subjected to protein microsequencing. The amino acid sequence obtained from microsequencing can be used to design unique or degenerate oligonucleotide probes to screen cDNA libraries to identify genes encoding the putative receptor molecule.

Polypeptides of the invention also can be used to access CKα-2 binding capacity of CKα-2 binding molecules, such as receptor molecules, in cells or in cell-free preparations.

The invention also provides a method of screening compounds to identify those which enhance or block the action of CKα-2 on cells, such as its interaction with CKα-2-binding molecules such as receptor molecules. An agonist is a compound which increases the natural biological functions of CKα-2 or which functions in a manner similar to CKα-2, while antagonists decrease or eliminate such functions.

For example, a cellular compartment, such as a membrane or a preparation thereof, such as a membrane-preparation, may be prepared from a cell that expresses a molecule that binds CKα-2, such as a molecule of a signaling or regulatory pathway modulated by CKα-2. The preparation is incubated with labeled CKα-2 in the absence or the presence of a candidate molecule which may be a CKα-2 agonist or antagonist. The ability of the candidate molecule to bind the binding molecule is reflected in decreased binding of the labeled ligand. Molecules which bind gratuitously, i.e., without inducing the effects of CKα-2 on binding the CKα-2 binding molecule, are most likely to be good antagonists. Molecules that bind well and elicit effects that are the same as or closely related to CKα-2 are agonists.

CKα-2-like effects of potential agonists and antagonists may be measured, for instance, by determining activity of a second messenger system following interaction of the candidate molecule with a cell or appropriate cell preparation, and comparing the effect with that of CKα-2 or molecules that elicit the same effects as CKα-2. Second messenger systems that may be useful in this regard include but are not limited to AMP guanylate cyclase, ion channel or phophoinositide hydrolysis second messenger systems.

Another example of an assay for CKα-2 antagonists is a competitive assay that combines CKα-2 and a potential antagonist with membrane-bound CKα-2 receptor molecules or recombinant CKα-2 receptor molecules under appropriate conditions for a competitive inhibition assay. CKα-2 can be labeled, such as by radioactivity, such that the number of CKα-2 molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing CKα-2-induced activities, thereby preventing the action of CKα-2 by excluding CKα-2 from binding.

Potential antagonists include a small molecule which binds to and occupies the binding site of the polypeptide thereby preventing binding to cellular binding molecules, such as receptor molecules, such that normal biological activity is prevented. Examples of small molecules include but are not limited to small organic molecules, peptides or peptide-like molecules.

Other potential antagonists include antisense molecules. Antisense technology can be used to control gene expression through antisense DNA or RNA or through triple-helix formation. Antisense techniques are discussed, for example, in Okano, *J. Neurochem.* 56:560 (1991); *Oligodeoxynucleotides As Antisense Inhibitors Of Gene Expression,* CRC Press, Boca Raton, Fla. (1988). Triple helix formation is discussed in, for instance Less et al., *Nucl. Acids Res.* 6:3073 (1979); Cooney et al., *Science* 241:456 (1988); and Dervan et al., *Science* 251:1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of CKα-2. The antisense RNA oligonucleotide hybridizes to the mRNA in vivo and blocks translation of the mRNA molecule into CKα-2 polypeptide. The oligonucleotides described above can also be delivered to cells such that the antisense RNA or DNA may be expressed in vivo to inhibit production of CKα-2.

The antagonists may be employed for instance to inhibit the chemotaxis and activation of macrophages and their precursors, and of neutrophils, basophils, B lymphocytes and some T cell subsets, e.g., activated and CD8 cytotoxic T cells and natural killer cells, in certain auto-immune and chronic inflammatory and infective diseases. Examples of auto-immune diseases include multiple sclerosis, and insulin-dependent diabetes.

The antagonists may also be employed to treat infectious diseases including silicosis, sarcoidosis, idiopathic pulmonary fibrosis by preventing the recruitment and activation of mononuclear phagocytes. They may also be employed to treat idiopathic hyper-cosinophilic syndrome by preventing eosinophil production and migration. Endotoxic shock may also be treated by the antagonists by preventing the migration of macrophages and their production of the human chemokine polypeptides of the present invention.

The antagonists may also be employed for treating atherosclerosis, by preventing monycyte infiltration in the artery wall.

The antagonists may also be employed to treat histamine-mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated.

The antagonists may also be employed to treat chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung.

Antagonists may also be employed to treat rheumatoid arthritis by preventing the attraction of monocytes into synovial fluid in the joints of patients. Monocyte influx and activation plays a significant role in the pathogenesis of both degenerative and inflammatory arthropathics.

The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-dependent fever induced by chemokines.

The antagonists may also be employed to treat cases of bone marrow failure, for example, aplastic anemia and myelodysplastic syndrome.

The antagonists may also be employed to treat asthma and allergy by preventing cosinophil accumulation in the lung. The antagonists may also be employed to treat subepithelial basement membrane fibrosis which is a prominent feature of the asthmatic lung.

The antagonists may be employed in a composition with a pharmaceutically acceptable carrier, e.g., as hereinafter described.

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 μg/kg body weight. In most cases they will be administered in an amount not in excess of about 8 mg/kg body weight per day. Preferably, in most cases, dose is from about 10 μg/kg to about 1 mg/kg body weight, daily. It will be appreciated that optimum dosage will be determined by standard methods for each treatment modality and indication, taking into account the indication, its severity, route of administration, complicating conditions and the like.

The CKα-2 polynucleotides, polypeptides, agonists and antagonists that are polypeptides may be employed in accordance with the present invention by expression of such polypeptides in vivo, in treatment modalities often referred to as "gene therapy."

Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct in a replication defective retroviral vector, as discussed above. The retroviral expression construct then may be isolated and introduced into a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virsu, and mammary tumor virus. In one embodiment, the retroviral plasmid vector is derived from Moloney Murine Leukemia Virus.

Such vectors well include one or more promoters for expressing the polypeptide. Suitable promoters which may be employed include, but are not limited to, the retroviral LTR; the SV40 promoter; and the human cytomegalovirus (CMV) promoter described in Miller et al., *Biotechniques* 7:980–990 (1989), or any other promoter (e.g., cellular promoters such as eukaryotic cellular promoters including, but not limited to, the histone, RNA polymerase III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptides of the present invention will be placed under the control of a suitable promoter. Suitable promoters which may be employed include, but are not limited to, adenoviral promoters, such as the adenoviral major late promoter, or heterologous promoters, such as the cytomegalovirsu (CMV) promoter; the respiratory syncytial virus (RSV) promoter; inducible promoters, such as the MMT promoter, the metallothionein promoter; heat shock promoters; the albumin promoter; the ApoAl promoter; human globin promoters; viral thymidine kinase promoters, such as the Herpes Simplex thymidine kinase promoter; retroviral LTRs (including the modified retroviral LTRs herein above described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Y-2, Y-AM, PA12, T19-14X, VT-19-17-H2, YCRE, YCRIP, GP+E-86, GP+envAm 12, and DAN cell lines as described in Miller, A., *Human Gene Therapy* 1:5–14 (1990). The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention. Certain terms used herein are explained in the foregoing glossary.

All examples were carried out using standard techniques, which are well known and routine to those of skill in the art, except where otherwise described in detail. All parts or amounts set out in the following examples are by weight, unless otherwise specified. Routine molecular biology techniques of the following examples can be carried out as described in standard laboratory manuals, such as Sambrook et al., *Molecular Cloning: A Laboratory Manual,* 2nd Ed.; Cold Spring Harbor Laboratory Press, Cold Spring Harbor, N.Y. (1989), herein referred to as "Sambrook,"

Unless otherwise stated size separation of fragments in the examples below was carried out using standard techniques of agarose and polyacrylamide gel electrophoresis ("PAGE") in Sambrook and numerous other references such as, for instance, by Goeddel et al., *Nucleic Acids Res.* 8:4057 (1980).

Unless described otherwise, ligations were accomplished using standard buffers, incubation temperatures and times, approximately equimolar amounts of the DNA fragments to be ligated and approximately 10 units of T4 DNA ligase ("ligase") per 0.5 μg of DNA.

EXAMPLE 1

Expression and Purification of Human CKα-2 Using Bacteria

The DNA sequence encoding a human CKα-2 protein encoded by the deposited polynucleotide was amplified using PCR oligonucleotide primers specific to the amino acid carboxyl terminal sequence of the mature form of the human CKα-2 protein shown in FIG. 1 (SEQ ID NO:2) and to vector sequences 3' to the gene. Additional nucleotides containing restriction sites to facilitate cloning were added to the 5' and 3' sequences respectively.

The 5' oligonucleotide primer had the sequence 5' CCC GCATGC CCG CGC GTG TGG ACG GG 3' (SEQ ID NO:5) containing the underlined SphI restriction site.

The 3' primer had the sequence 5' CCC GGATCC CTA TTC TTC GTA GAA CCT 3'(SEQ ID NO:6) containing the underlined BamHI restriction site.

The restrictions sites were convenient to restriction enzyme sites in the bacterial expression vectors pQE-9 which were used for bacterial expression in these examples. (Qiagen, Inc. 9259 Eton Avenue, Chatsworth, Calif. 91311). pQE-9 encodes ampicillin antibiotic resistance ("Amp$^r$") and contains a bacterial origin of replication ("ori"), an IPTG inducible promoter, a ribosome binding site ("RBS"), a 6-His tag and restriction enzyme sites.

The amplified human CKα-2 DNA and the vector pQE-9 both were digested with SphI and BamHI and the digested DNAs then were ligated together. Insertion of the CKα-2 DNA into the restricted vector placed the CKα-2 coding region downstream of and operably linked to the vector's IPTG-inducible promoter and in-frame with an initiating AUG appropriately positioned for translation of CKα-2.

The ligation mixture was transformed into competent *E. coli* cells using standard procedures. Such procedures are described in Sambrook et al., *Molecular Cloning: A Laboratory Manual*, 2nd Ed., Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan$^r$"), was used in carrying out the illustrative example described here. This strain, which is only one of many that are suitable for expressing CKα-2, is available commercially from Qiagen.

Transformants were identified by their ability to grow on LB plates in the presence of ampicillin. Plasmid DNA was isolated from resistant colonies and the identity of the cloned DNA was confirmed by restriction analysis.

Clones containing the desired constructs were grown overnight ("O/N") in liquid culture in LB media supplemented with both ampicillin (100 μg/ml) and kanamycin (25 μg/ml).

The O/N culture was used to inoculate a large culture, at a dilution of approximately 1:100 to 1:250. The cells were grown to an optical density at 600 nm ("$OD_{600}$") of between 0.4 and 0.6. Isopropyl-B-D-thiogalactopyranoside ("IPTG") was then added to a final concentration of 1 mM to induce transcription from lac repressor sensitive promoters, by inactivating the lacI repressor. Cells subsequently were incubated further for 3 to 4 hours. Cells then were harvested by centrifugation and disrupted, by standard methods. Inclusion bodies were purified from the disrupted cells using routine collection techniques, and protein was solubilized from the inclusion bodies into 8M urea. The 8M urea solution containing the solubilized protein was passed over a PD-10 column in 2X phosphate buffered saline ("PBS"), thereby removing the urea, exchanging the buffer and refolding the protein. The protein was purified by a further step of chromatography to remove endotoxin. Then, it was sterile filtered. The sterile filtered protein preparation was stored in 2X PBS at a concentration of 95 micrograms per mL.

EXAMPLE 2

Cloning and Expression of Human CKα-2 in a Baculovirus Expression System

The cDNA sequence encoding the full length human CKα-2 protein shown in FIG. 1 (SEQ ID NO:2) and encoded by the deposited clone is amplified using PCR oligonucleotide primers corresponding to the 5' and 3' sequences of the gene.

The 5' primer has the sequence 5' GCC GGATCC GCC ATC ATG TCC CTG CTC CC 3' (SEQ ID NO:7) containing the underlined BamHI restriction enzyme. Inserted into an expression vector, as described below, the 5' end of the amplified fragment encoding human CKα-2 provides an efficient signal peptide. An efficient signal for initiation of translation in eukaryotic cells, as described by Kozak, M., *J. Mol. Biol.* 196:947–950 (1987) is appropriately located in the vector portion of the construct.

The 3' primer has the sequence 5' CGC GTCTAGACT ATT CTT CGT AGA ACC T 3' (SEQ ID NO:8) containing the underlined XbaI restriction site.

The amplified fragment is isolated from a 1% agarose gel using a commercially available kit ("Geneclean," BIO 101 Inc., La Jolla, Calif.). The fragment then is digested with BamHI and Asp718 and again is purified on a 1% agarose gel. This fragment is designated herein F2.

The vector pRG1 is used to express the CKα-2 protein in the baculovirus expression system, using standard methods, such as those described in Summers et al., *A Manual of Methods For Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites. The polyadenylation site of the simian virus 40 ("SV40") is used for efficient polyadenylation. For an easy selection of recombinant virus the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of PRG1, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., *Virology* 170:31–39, among others.

The plasmid is digested with the restriction enzymes XbaI and BamHI and then is dephosphorylated using calf intestinal phosphatase, using routine procedures known in the art.

The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 are ligated together with T4 DNA ligase. *E. coli* HB101 cells are transformed with ligation mix and spread on culture plates. Bacteria are identified that contain the plasmid with the human CKα-2 gene by digesting DNA from individual colonies using XbaI and BamHI and then analyzing the digestion product by gel electrophoresis. The sequence of the cloned fragment is confirmed by DNA sequencing. This plasmid is designated herein pBacCKα-2.

5 μg of the plasmid pBacCKα-2 is co-transfected with 1.0 μg of a commercially available linearized baculovirus DNA ("BaculoGold™ baculovirus DNA", Pharmingen, San Diego, Calif.), using the lipofection method described by Felgner et al., *Proc. Natl. Acad. Sci. (USA)* 84:7413–7417 (1987). 1 μg of BaculoGold™ virus DNA and 5 μg of the plasmid pBacCKα-2 are mixed in a sterile well of a microtiter plate containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-strained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 nun dishes. Four days later the supernatants of these culture dishes are harvested and then they are stored at 4° C. A clone containing properly inserted CKα-2 is identified by DNA analysis including restriction mapping and sequencing. This is designated herein as V-CKα-2.

Sf9 cells are grown in Grace's medium supplemented with 10% heat-inactivated FBS. The cells are infected with the recombinant baculovirus V-CKα-2 at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 μCi of $^{35}$S-methionine and 5 μCi $^{35}$S cysteine (available from Amersham) are added. The cells are further incubated for 16 hours and then they are harvested by centrifugation, lysed and the labeled proteins are visualized by SDS-PAGE and autoradiography.

EXAMPLE 3

Expression of CKα-2 in COS Cells

The expression plasmid, CKα-2 HA, is made by cloning a cDNA encoding the CKα-2 shown in FIG. 1 (SEQ ID NO:2) into the expression vector pcDNAI/Amp (which can be obtained from Invitrogen, Inc.).

The expression vector pcDNAI/amp contains: (1) an *E. coli* origin of replication effective for propagation in *E. coli* and other prokaryotic cell; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the entire CKα-2 precursor and a HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., *Cell* 37:767 (1984). The fusion of the HA tag to the target protein allows easy detection of the recombinant protein with an antibody that recognizes the HA epitope.

The plasmid construction strategy is as follows. The CKα-2 cDNA of the deposit clone is amplified using primers that contained convenient restriction sites, much as described above regarding the construction of expression vectors for expression of CKα-2 in *E. coli* and *S. furgiperda*. To facilitate detection, purification and characterization of the expressed CKα-2, one of the primers contains a haemaglutinin tag ("HA tag") as described above.

Suitable primers include that following, which are used in this example. The 5' primer, containing the underlined BamHI site, has the following sequence: 5' AAA <u>GGATCC</u> ATG TCC CTG CTC CCA CGC CGC 3' (SEQ ID NO:9).

The 3' primer, containing the underlined XbaI site, has the following sequence:

```
5' CGC TCT AGA TCA AGC GTA GTC TGG    (SEQ ID NO:10)
GAC GTC GTA TGG GTA TTC TTC GTA GAA
CCT GCG 3'.
```

The PCR amplified DNA fragment and the vector, pcDNAI/Amp, are digested with and then ligated. The ligation mixture is transformed into *E. coli* strain SURE (available from Stratagene Cloning Systems, La Jolla, Calif.) the transformed culture is plated on ampicillin media plates which then are incubated to allow growth of ampicillin resistant colonies. Plasmid DNA is isolated from resistant colonies and examined by restriction analysis and gel sizing for the presence of the CKα-2-encoding fragment.

For expression of recombinant CKα-2, COS cells are transfected with an expression vector, as described above, using DEAE-DEXTRAN, as described, for instance, in Sambrook et al., *Molecular Cloning: A Laboratory Manual*, Cold Spring Laboratory Press, Cold Spring Harbor, N.Y. (1989).

Cells are incubated under conditions for expression of CKα-2 by the vector.

Expression of the CKα-2 HA fusion protein is detected by radiolabelling and immunoprecipitation, using methods described in, for example Harlow et al., *Antibodies: A*

*Laboratory Manual,* 2nd Ed., Cold Spring Harbor Laboratory Press, Cold Spring Harbor, N.Y. (1989). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 01% SDS, 1% NP-40, 0.5% DOC, 50 mM TRIS, pH 7.5, as described by Wilson et al., cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

EXAMPLE 4

Tissue Distribution of CKα-2 Expression

Northern blot analysis is carried out to examine the levels of expression of CKα-2 in human tissues, using methods described by, among others, Sambrook et al., cited above. Total cellular RNA samples are isolated with RNAzol™ B system (Biotccx Laboratories, Inc. 6023 South Loop East, Houston, Tex. 77033).

About 10 μg of total RNA is isolated from tissue samples. The RNA is size resolved by electrophoresis through a 1% agarose gel under strongly denaturing conditions. RNA is blotted from the gel onto a nylon filter, and the filter then is prepared for hybridization to a detectably labeled polynucleotide probe.

As a probe to detect mRNA that encodes CKα-2, the antisense strand of the coding region of the cDNA insert in the deposited clone is labeled to a high specific activity. The cDNA is labeled by primer extension, using the Prime-It kit, available from Strategene. The reaction is carried out sing 50 ng of the cDNA, following the standard reaction protocol as recommended by the supplier. The labeled polynucleotide is purified away from other labeled reaction components by column chromatography using a Select-G-50 column, obtained from 5-Prime-3-Prime, Inc. of 5603 Arapahoe Road, Boulder, Colo. 80303.

The labeled probe is hybridized to the filter, at a concentration of 1,000,000 cpm/ml, in a small volume of 7% SDS, 0.5 M NaPO$_4$, pH 7.4 at 65° C., overnight.

Thereafter the probe solution is drained and the filter is washed twice at room temperature and twice at 60° C. with 0.5×SSC, 0.1% SDS. The filter then is dried and exposed to film at −70° C. overnight with an intensifying screen.

Autoradiography shows that mRNA for CKα-2 is abundant in small intestine.

EXAMPLE 5

Gene Therapeutic Expression of Human CKα-2

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted—the chunks of tissue remain fixed to the bottom of the flask—and fresh media is added (e.g., Ham's F12 media, with 10% FBS, penicillin and streptomycin). The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy is digested with restriction enzymes for cloning a fragment to be expressed. The digested vector is treated with calf intestinal phosphatase to prevent self-ligation. The dephosphorylated, linear vector is fractionated on an agarose gel and purified.

Human cDNA capable of expressing active CKα-2, is isolated. The ends of the fragment are modified, if necessary, for cloning into the vector. For instance, 5' overhanging may be treated with DNA polymerase to create blunt ends. 3' overhanging ends may be removed using SI nuclease. Linkers may be ligated to blunt ends with T4 DNA ligase.

Equal quantities of the Moloney murine leukemia virus linear backbone and the CKα-2 fragment are mixed together and joined using T4 DNA ligase. The ligation mixture is used to transform *E. coli* and the bacteria are then plated onto agar-containing kanamycin. Kanamycin phenotype and restriction analysis confirm that the vector has the properly inserted gene.

Packaging cells are grown in tissue culture to confluent density in Dulbecco's Modified Eagle's Medium (DMEM) with 10% calf serum (CS), penicillin and streptomycin. The vector containing the CKα-2 gene is introduced into the packaging cells by standard techniques. Infectious viral particles containing the CKα-2 gene are collected from the packaging cells, which now are called producer cells.

Fresh media is added to the producer cells, and after an appropriate incubation period media is harvested from the plates of confluent producer cells. The media, containing the infectious viral particles, is filtered through a Millipore filter to remove detached producer cells. The filtered media then is used to infect fibroblast cells. Media is removed from a sub-confluent plate of fibroblasts and quickly replaced with the filtered media. Polybrene (Aldrich) may be included in the media to facilitate transduction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Engineered fibroblasts then may be injected into rats, either alone or after having been grown to confluence on microcarrier beads, such as cytodex 3 beads. The injected fibroblasts produce CKα-2 product, and the biological actions of the protein are conveyed to the host.

It will be clear that the invention may be practiced otherwise than as particularly described in the foregoing description and examples. Numerous modifications and variations of the present invention are possible in light of the above teachings and, therefore, are within the scope of the appended claims.

What is claimed is:

1. An isolated antibody or fragment thereof that specifically binds to a protein selected from the group consisting of:
   (a) a protein whose amino acid sequence consists of amino acid residues 1 to 111 of SEQ ID NO:2;
   (b) a protein whose amino acid sequence consists of amino acid residues 29 to 111 of SEQ ID NO:2;
   (c) a protein whose amino acid sequence consists of a portion of SEQ ID NO:2, wherein said portion is at least 30 contiguous amino acid residues in length; and
   (d) a protein whose amino acid sequence consists of a portion of SEQ ID NO:2, wherein said portion is at least 50 contiguous amino acid residues in length.

2. The antibody or fragment thereof of claim 1 that specifically binds protein (a).

3. The antibody or fragment thereof of claim 1 that specifically binds protein (b).

4. The antibody or fragment thereof of claim 1 that specifically binds protein (c).

5. The antibody or fragment thereof of claim 1 that specifically binds protein (d).

6. The antibody or fragment thereof of claim 2 that specifically binds protein (b).

7. The antibody or fragment thereof of claim 3 wherein said protein bound by said antibody or fragment thereof is glycosylated.

8. The antibody or fragment thereof of claim 3 wherein said antibody or fragment thereof is human.

9. The antibody or fragment thereof of claim 3 wherein said antibody or fragment thereof is polyclonal.

10. The antibody or fragment thereof of claim 3 wherein said antibody or fragment thereof is monoclonal.

11. The antibody or fragment thereof of claim 3 which is selected from the group consisting of:
    (a) a chimeric antibody or fragment thereof;
    (b) a humanized antibody or fragment thereof;
    (c) a single chain antibody; and
    (d) a Fab fragment.

12. The antibody or fragment thereof of claim 3 which is labeled.

13. The antibody or fragment thereof of claim 3 wherein said antibody or fragment thereof specifically binds to said protein in a Western blot or an ELISA.

14. An isolated cell that produces the antibody or fragment thereof of claim 3.

15. A hybridoma that produces the antibody or fragment thereof of claim 3.

16. A method of detecting CKα-2 protein in a biological sample comprising:
    (a) contacting the biological sample with the antibody or fragment thereof of claim 3; and
    (b) detecting the CKα-2 protein in the biological sample.

17. An isolated antibody or fragment thereof that specifically binds to a protein selected from the group consisting of:
    (a) a protein whose amino acid sequence consists of the amino acid sequence of the full-length polypeptide encoded by the cDNA contained in ATCC Deposit Number 97400;
    (b) a protein whose amino acid sequence consists of the amino acid sequence of the mature form of the polypeptide encoded by the cDNA contained in ATCC Deposit Number 97400;
    (c) a protein whose amino acid sequence consists of the amino acid sequence of a portion of the polypeptide encoded by the cDNA contained in ATCC Deposit Number 97400, wherein said portion is at least 30 contiguous amino acid residues in length; and (d) a protein whose amino acid sequence consists of the amino acid sequence of a portion of the polypeptide encoded by the cDNA contained in ATCC Deposit Number 97400, wherein said portion is at least 50 contiguous amino acid residues in length.

18. The antibody or fragment thereof of claim 17 that specifically binds protein (a).

19. The antibody or fragment thereof of claim 17 that specifically binds protein (b).

20. The antibody or fragment thereof of claim 17 that specifically binds protein (c).

21. The antibody or fragment thereof of claim 17 that specifically binds protein (d).

22. The antibody or fragment thereof of claim 18 that specifically binds protein (b).

23. The antibody or fragment thereof of claim 19 wherein said protein bound by said antibody or fragment thereof is glycosylated.

24. The antibody or fragment thereof of claim 19 wherein said antibody or fragment thereof is human.

25. The antibody or fragment thereof of claim 19 wherein said antibody or fragment thereof is polyclonal.

26. The antibody or fragment thereof of claim 19 wherein said antibody or fragment there of is monoclonal.

27. The antibody or fragment thereof of claim 19 which is selected from the group consisting of:
   (a) a chimeric antibody or fragment thereof;
   (b) a humanized antibody or fragment thereof;
   (c) a single chain antibody; and
   (d) a Fab fragment.

28. The antibody or fragment thereof of claim 19 which is labeled.

29. The antibody or fragment thereof of claim 19 wherein said antibody or fragment thereof specifically binds to said protein in a Western blot or an ELISA.

30. An isolated cell that produces the antibody or fragment thereof of claim 19.

31. A hybridoma that produces the antibody or fragment thereof of claim 19.

32. A method of detecting CKα-2 protein in a biological sample comprising:
   (a) contacting the biological sample with the antibody or fragment thereof of claim 19; and
   (b) detecting the CKα-2 protein in the biological sample.

33. An isolated antibody or fragment thereof that specifically binds a CKα-2 protein purified from a cell culture wherein said CKα-2 protein is encoded by a polynucleotide encoding amino acids −28 to 83 of SEQ ID NO:2.

34. The antibody or fragment thereof of claim 33 wherein said antibody or fragment thereof is monoclonal.

35. The antibody or fragment thereof of claim 33 wherein said antibody or fragment thereof is polyclonal.

36. The antibody or fragment thereof of claim 33 wherein said antibody or fragment thereof is human.

37. The antibody or fragment thereof of claim 33 which is selected from the group consisting of:
   (a) a chimeric antibody or fragment thereof;
   (b) a humanized antibody or fragment thereof;
   (c) a single chain antibody; and
   (d) a Fab fragment.

38. The antibody or fragment thereof of claim 33 wherein said antibody or fragment thereof specifically binds to said protein in a Western blot or an ELISA.

39. The antibody or fragment thereof of claim 33 wherein the amino acid sequence of said CKα-2 protein consists of amino acid residues 1 to 83 of SEQ ID NO:2.

* * * * *

UNITED STATES PATENT AND TRADEMARK OFFICE
CERTIFICATE OF CORRECTION

PATENT NO. : 7,122,639 B2 Page 1 of 1
APPLICATION NO. : 10/267900
DATED : October 17, 2006
INVENTOR(S) : Ni et al.

It is certified that error appears in the above-identified patent and that said Letters Patent is hereby corrected as shown below:

On the Title page,

Item [*] Notice and Item 45:    Subject to any disclaimer, the term of this patent is extended or adjusted under 35 USC 154(b) by (394) days Delete the phrase "by 394" and insert -- by 514 days--

Signed and Sealed this

Sixteenth Day of October, 2007

JON W. DUDAS
*Director of the United States Patent and Trademark Office*